United States Patent
Jepson et al.

(10) Patent No.: US 8,486,044 B2
(45) Date of Patent: Jul. 16, 2013

(54) PORT ASSEMBLY FOR USE WITH NEEDLELESS CONNECTOR

(75) Inventors: Steven C. Jepson, Vernon Hills, IL (US);
Gilbert Semaan, Palatine, IL (US);
David D. Hsu, Skokie, IL (US); James B. Winje, Franklin Park, IL (US);
Richard F. Chamernik, Beach Park, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 828 days.

(21) Appl. No.: 12/613,960

(22) Filed: Nov. 6, 2009

(65) Prior Publication Data
US 2010/0108681 A1 May 6, 2010

Related U.S. Application Data

(63) Continuation-in-part of application No. 12/194,137, filed on Aug. 19, 2008, now Pat. No. 8,062,280, and a continuation of application No. PCT/US2009/054185, filed on Aug. 18, 2009.

(51) Int. Cl.
*A61M 5/32* (2006.01)
(52) U.S. Cl.
USPC .......................... 604/415; 604/403; 604/411
(58) Field of Classification Search
USPC .................................... 604/403–416
See application file for complete search history.

(56) References Cited

U.S. PATENT DOCUMENTS

| | | | |
|---|---|---|---|
| 3,368,560 | A | 2/1968 | Gewecke |
| 3,509,879 | A | 5/1970 | Bathish et al. |
| 3,915,212 | A | 10/1975 | Bujan et al. |

(Continued)

FOREIGN PATENT DOCUMENTS

| | | |
|---|---|---|
| CA | 2386830 | 9/2009 |
| DE | 29800107 | 3/1998 |

(Continued)

OTHER PUBLICATIONS

International Search Report and Written Opinion for corresponding International Application No. PCT/US2009/054185, dated May 3, 2010 (11 pages).
Partial International Search Report for corresponding International Application No. PCT/US2009/054185, dated Dec. 22, 2009 (2 pp.).
Baxter Healthcare Corporation, Clearlink Brochure (Aug. 2007) (2 pages).

(Continued)

*Primary Examiner* — Philip R Wiest
*Assistant Examiner* — Ariana Zimbouski
(74) *Attorney, Agent, or Firm* — Marshall, Gerstein & Borun LLP

(57) ABSTRACT

A port assembly includes a housing with an opening and a bore therethrough, a slit septum disposed in the opening to control access through the opening, a base joined to the housing and having a membrane attached thereto, a perforator having a first end abutting the slit septum and a second end aligned with the membrane, and a resilient member disposed between the perforator and the base. The perforator has first and second lumens, the first lumen extending between the first and second ends of the perforator and the second lumen extending between a point between the first and second ends and the second end. The perforator also has a seal disposed about the first lumen at the first end of the perforator, and a valve associated with the second lumen to limit flow of fluid through the second lumen in the direction of the second end.

17 Claims, 25 Drawing Sheets

U.S. PATENT DOCUMENTS

| | | |
|---|---|---|
| 3,977,555 A | 8/1976 | Larson |
| 4,181,140 A | 1/1980 | Bayham et al. |
| 4,187,893 A | 2/1980 | Bujan |
| 4,270,534 A | 6/1981 | Adams |
| 4,294,247 A | 10/1981 | Carter et al. |
| 4,340,049 A | 7/1982 | Munsch |
| 4,386,622 A | 6/1983 | Munsch |
| 4,410,321 A | 10/1983 | Pearson et al. |
| 4,411,662 A | 10/1983 | Pearson |
| 4,432,755 A | 2/1984 | Pearson |
| 4,435,179 A | 3/1984 | Walker et al. |
| 4,458,733 A | 7/1984 | Lyons |
| 4,479,989 A | 10/1984 | Mahal |
| 4,484,351 A | 11/1984 | de Leeuwe et al. |
| 4,507,114 A | 3/1985 | Bohman et al. |
| 4,583,971 A | 4/1986 | Bocquet et al. |
| 4,586,928 A | 5/1986 | Barnes et al. |
| 4,589,879 A | 5/1986 | Pearson |
| 4,637,934 A | 1/1987 | White |
| 4,722,727 A | 2/1988 | Ogden et al. |
| 4,785,859 A | 11/1988 | Gustavsson et al. |
| 4,846,795 A | 7/1989 | Minagawa et al. |
| 5,006,114 A | 4/1991 | Rogers et al. |
| 5,065,783 A | 11/1991 | Ogle, II |
| 5,122,123 A | 6/1992 | Vaillancourt |
| 5,269,771 A | 12/1993 | Thomas et al. |
| 5,304,163 A | 4/1994 | Bonnici et al. |
| 5,308,347 A | 5/1994 | Sunago et al. |
| 5,330,464 A | 7/1994 | Mathias et al. |
| 5,334,180 A | 8/1994 | Adolf et al. |
| 5,380,315 A | 1/1995 | Isono et al. |
| 5,391,150 A | 2/1995 | Richmond |
| 5,514,123 A | 5/1996 | Adolf et al. |
| 5,533,994 A | 7/1996 | Meyer et al. |
| 5,540,674 A | 7/1996 | Karas et al. |
| 5,685,866 A | 11/1997 | Lopez |
| 5,700,248 A | 12/1997 | Lopez |
| 5,730,418 A | 3/1998 | Feith et al. |
| 5,738,663 A | 4/1998 | Lopez |
| 5,782,816 A | 7/1998 | Werschmidt et al. |
| 5,785,693 A | 7/1998 | Haining |
| 5,810,398 A | 9/1998 | Matkovich |
| 5,873,862 A | 2/1999 | Lopez |
| 5,901,942 A | 5/1999 | Lopez |
| 5,902,298 A | 5/1999 | Niedospial, Jr. et al. |
| 5,928,204 A | 7/1999 | Lopez |
| 5,931,829 A * | 8/1999 | Burbank et al. ............... 604/502 |
| 6,019,748 A | 2/2000 | Lopez |
| 6,029,946 A | 2/2000 | Doyle |
| 6,032,926 A | 3/2000 | Fuchs |
| 6,050,978 A | 4/2000 | Orr et al. |
| 6,113,068 A | 9/2000 | Ryan |
| 6,113,583 A | 9/2000 | Fowles et al. |
| 6,126,618 A | 10/2000 | Bischof |
| 6,132,403 A | 10/2000 | Lopez |
| 6,132,404 A | 10/2000 | Lopez |
| 6,132,413 A | 10/2000 | Mathias et al. |
| 6,156,025 A | 12/2000 | Niedospial, Jr. et al. |
| 6,179,821 B1 | 1/2001 | Caspary et al. |
| 6,245,048 B1 | 6/2001 | Fangrow, Jr. et al. |
| 6,280,431 B1 | 8/2001 | Domkowski et al. |
| 6,290,206 B1 | 9/2001 | Doyle |
| 6,299,131 B1 | 10/2001 | Ryan |
| 6,325,782 B1 | 12/2001 | Lopez |
| 6,394,992 B1 | 5/2002 | Sjoholm et al. |
| 6,428,520 B1 | 8/2002 | Lopez et al. |
| 6,485,479 B1 | 11/2002 | Knierbein et al. |
| 6,491,679 B1 | 12/2002 | Okamoto et al. |
| 6,541,802 B2 | 4/2003 | Doyle |
| 6,572,592 B1 | 6/2003 | Lopez |
| 6,585,229 B2 | 7/2003 | Cote, Sr. et al. |
| 6,599,273 B1 | 7/2003 | Lopez |
| 6,635,043 B2 | 10/2003 | Lopez |
| 6,651,956 B2 | 11/2003 | Miller |
| 6,655,655 B1 | 12/2003 | Matkovich et al. |
| 6,681,946 B1 | 1/2004 | Jansen et al. |
| 6,726,672 B1 * | 4/2004 | Hanly et al. ................. 604/414 |
| 6,745,998 B2 | 6/2004 | Doyle |
| 6,758,833 B2 | 7/2004 | Lopez |
| 6,840,501 B2 | 1/2005 | Doyle |
| 6,869,426 B2 | 3/2005 | Ganem |
| 6,875,203 B1 | 4/2005 | Fowles et al. |
| 6,932,795 B2 | 8/2005 | Lopez et al. |
| 6,945,417 B2 | 9/2005 | Jansen et al. |
| 6,955,669 B2 | 10/2005 | Curutcharry et al. |
| 7,004,934 B2 | 2/2006 | Vaillancourt |
| 7,025,389 B2 | 4/2006 | Cuschieri et al. |
| 7,037,302 B2 | 5/2006 | Vaillancourt et al. |
| 7,074,216 B2 | 7/2006 | Fowles et al. |
| 7,100,890 B2 | 9/2006 | Cote, Sr. et al. |
| 7,350,669 B2 | 4/2008 | Rani |
| 7,350,764 B2 | 4/2008 | Raybuck |
| 7,396,051 B2 | 7/2008 | Baldwin et al. |
| 7,396,348 B2 | 7/2008 | Newton et al. |
| 7,425,209 B2 | 9/2008 | Fowles et al. |
| 7,470,265 B2 * | 12/2008 | Brugger et al. ............... 604/412 |
| 8,167,863 B2 * | 5/2012 | Yow ............................. 604/406 |
| 2002/0024036 A1 | 2/2002 | Rohrbough et al. |
| 2003/0093061 A1 | 5/2003 | Ganem |
| 2004/0073174 A1 | 4/2004 | Lopez |
| 2004/0122414 A9 | 6/2004 | Hurst et al. |
| 2004/0186458 A1 | 9/2004 | Hiejima et al. |
| 2004/0199139 A1 | 10/2004 | Fowles et al. |
| 2004/0206924 A1 | 10/2004 | Newton et al. |
| 2004/0243070 A1 | 12/2004 | Lopez |
| 2005/0090805 A1 | 4/2005 | Shaw et al. |
| 2005/0137566 A1 | 6/2005 | Fowles et al. |
| 2005/0222541 A1 | 10/2005 | Lopez et al. |
| 2006/0106360 A1* | 5/2006 | Wong ........................... 604/411 |
| 2006/0200087 A1 | 9/2006 | Lopez |
| 2006/0200091 A1 | 9/2006 | Lopez |
| 2006/0200092 A1 | 9/2006 | Lopez |
| 2006/0200093 A1 | 9/2006 | Lopez |
| 2006/0206058 A1 | 9/2006 | Lopez |
| 2006/0206059 A1 | 9/2006 | Lopez |
| 2006/0206060 A1 | 9/2006 | Lopez |
| 2006/0206061 A1 | 9/2006 | Lopez et al. |
| 2006/0229572 A1 | 10/2006 | Lopez |
| 2006/0264845 A1 | 11/2006 | Lopez |
| 2006/0264846 A1 | 11/2006 | Lopez |
| 2006/0264847 A1 | 11/2006 | Lopez |
| 2006/0264849 A1 | 11/2006 | Lopez et al. |
| 2006/0287638 A1 | 12/2006 | Aneas |
| 2007/0007478 A1 | 1/2007 | Leinsing et al. |
| 2007/0012893 A1 | 1/2007 | Lee et al. |
| 2007/0021721 A1 | 1/2007 | Lopez |
| 2007/0038189 A1* | 2/2007 | Bartholomew ............... 604/249 |
| 2007/0066965 A1 | 3/2007 | Coambs et al. |
| 2007/0173783 A1 | 7/2007 | Haindl |
| 2007/0253257 A1* | 11/2007 | Wang ....................... 365/185.29 |
| 2007/0299419 A1 | 12/2007 | Vancaillie et al. |
| 2008/0140021 A1 | 6/2008 | Richmond |
| 2008/0172024 A1 | 7/2008 | Yow |
| 2008/0190485 A1 | 8/2008 | Guala |
| 2008/0228163 A1 | 9/2008 | Smith |
| 2009/0270832 A1 | 10/2009 | Vancaillie et al. |
| 2010/0049160 A1 | 2/2010 | Jepson et al. |
| 2010/0108681 A1 | 5/2010 | Jepson et al. |

FOREIGN PATENT DOCUMENTS

| | | |
|---|---|---|
| EP | 0811797 | 12/1997 |
| WO | WO 97/43573 | 11/1997 |
| WO | WO 01/32524 | 5/2001 |
| WO | WO 2006/062912 | 6/2006 |

OTHER PUBLICATIONS

Edward Lifesciences LLC, VAMP and VAMP Jr. System Brochure (2002) (4 pages).
ICU Medical, Inc., CLC2000® Brochure (circa Jun. 2007) (2 pages).
I-Flow Corporation, One Step KVO™ Brochure (Jan. 1999) (2 pages).
Maximus Medical, MaxPlus Brochure, (circa Apr. 2007) (2 pages).

* cited by examiner

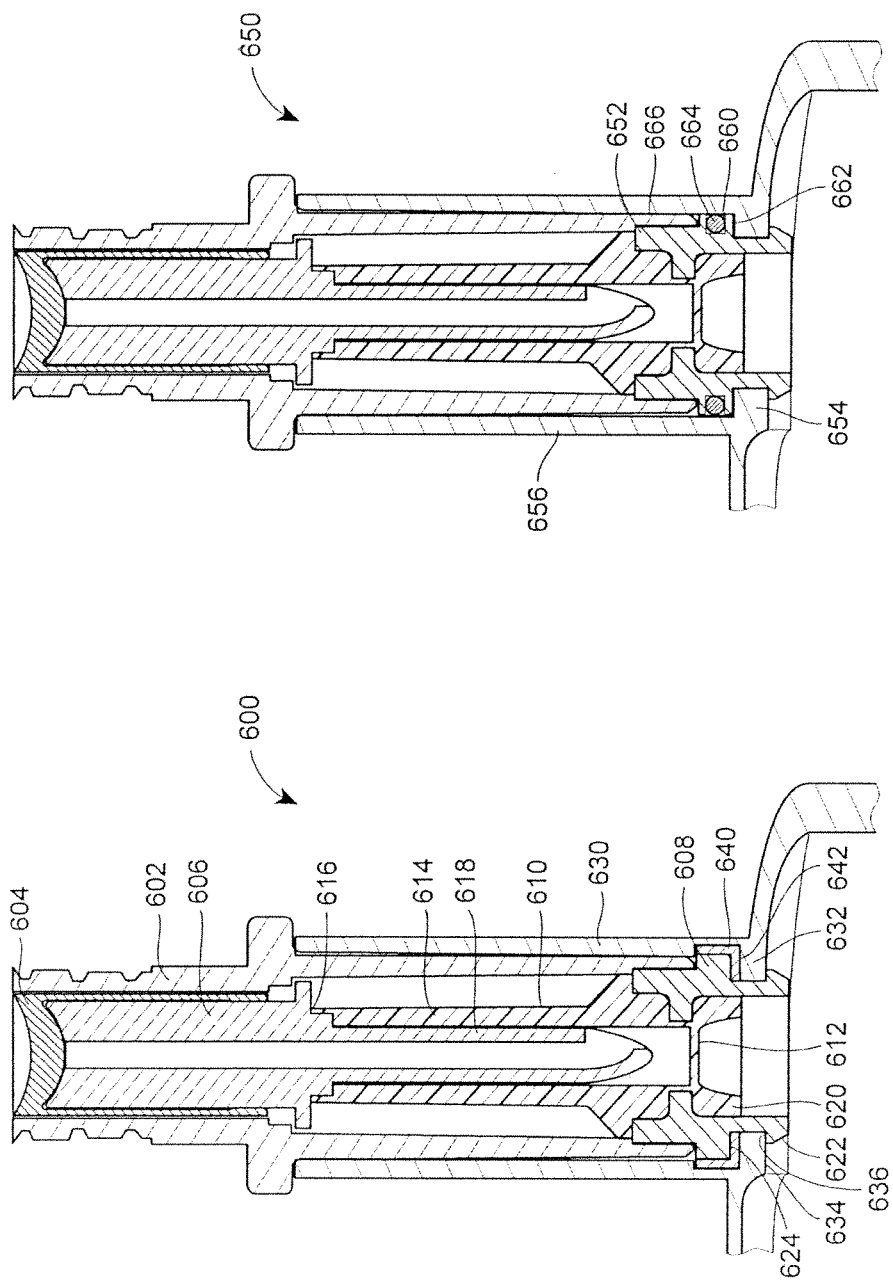

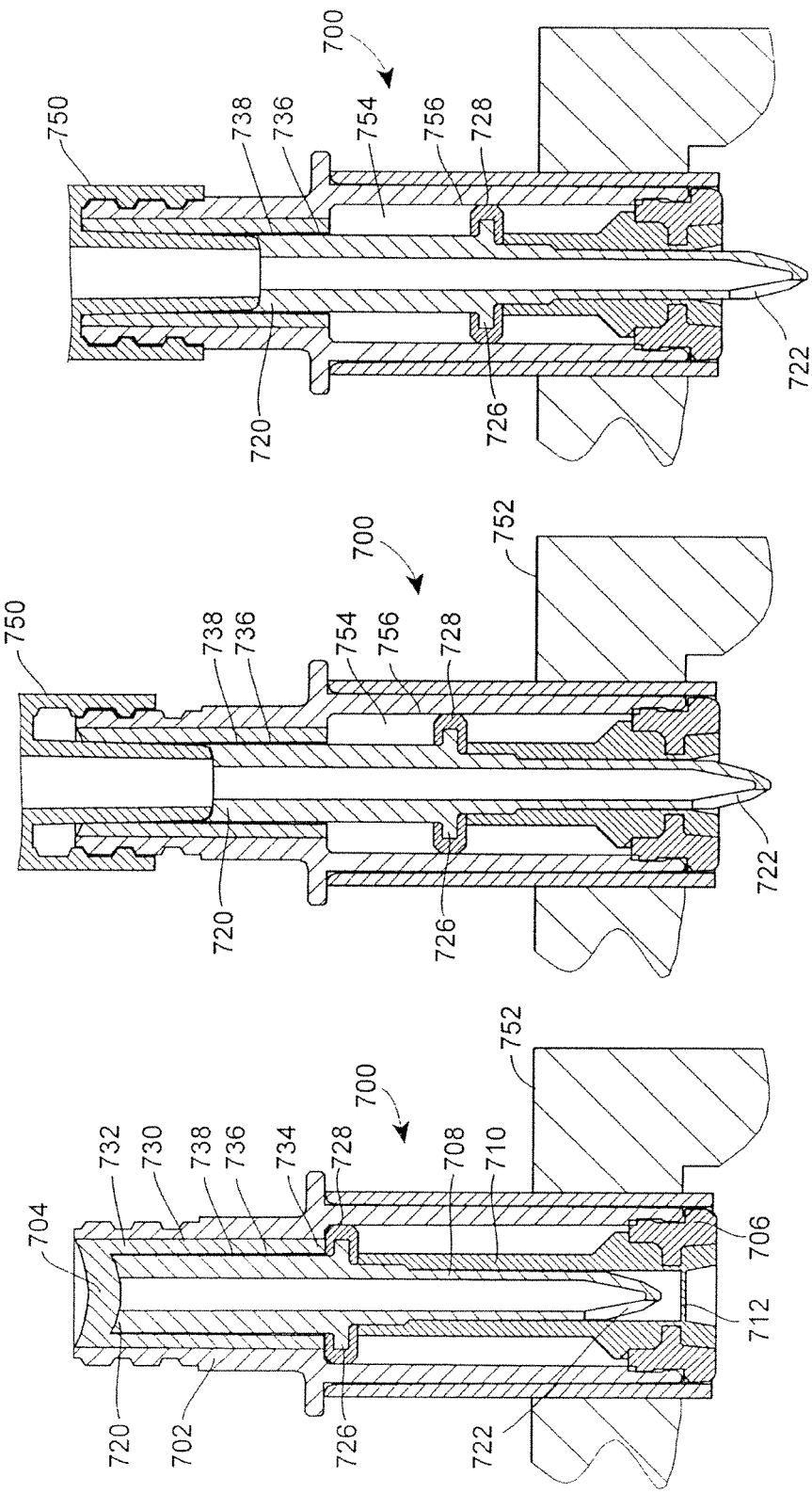

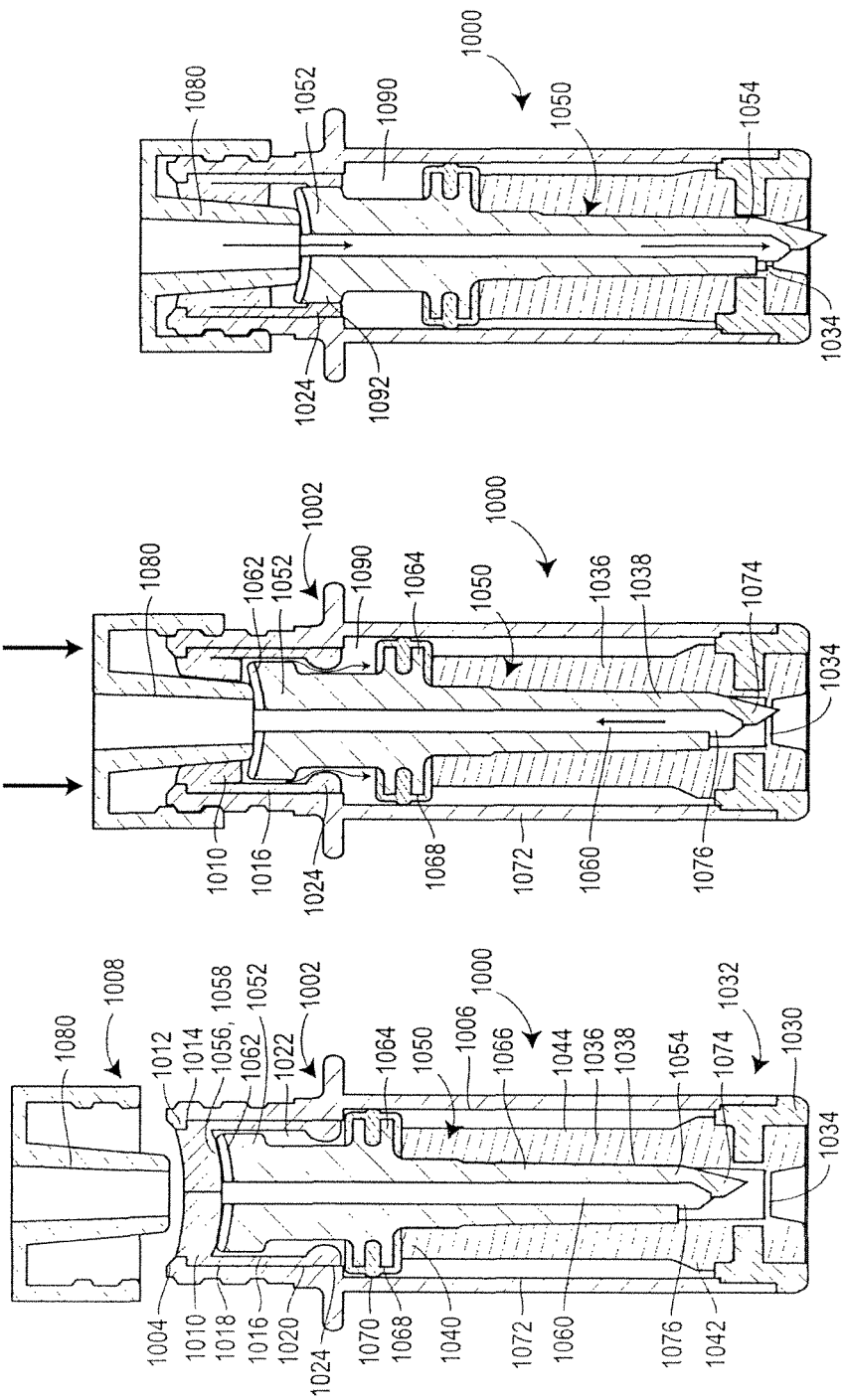

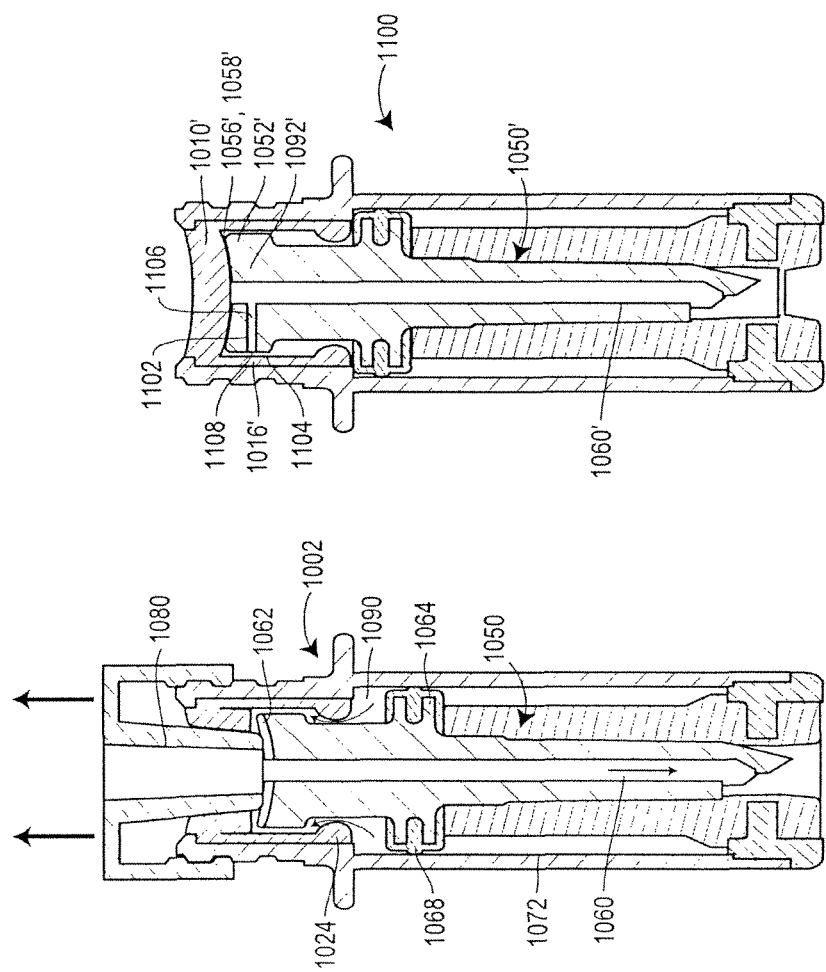

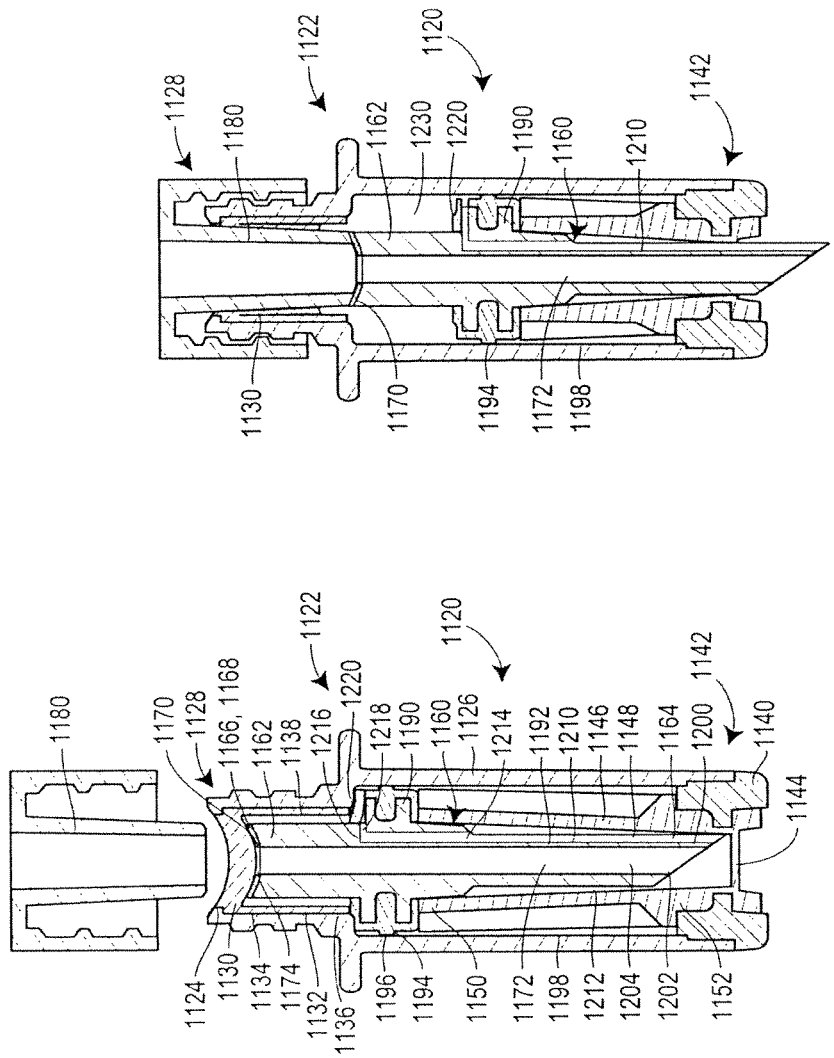

PORT ASSEMBLY FOR USE WITH NEEDLELESS CONNECTOR

This application is a continuation-in-part of U.S. application Ser. No. 12/194,137, filed Aug. 19, 2008, and a continuation of International Application No. PCT/US09/54185, filed Aug. 18, 2009, both of which are hereby incorporated by reference in their entirety in the present application.

BACKGROUND

This patent is directed to a port assembly for use with a needleless connector, and, in particular, to a port assembly for use with a needleless connector wherein the port assembly includes an axial perforator.

Intravenous ("I.V.") therapy involves the delivery of fluids to a patient through a vein. For example, a catheter is placed into the vein of the patient, and then fluids are administered to the patient through the catheter. Typically, the catheter is connected to an administration set in communication with a container, such as a flexible container or bag, from which fluids are infused into the patient.

The flexible container conventionally has two ports, an administration port ("admin port") and a medication port ("med port"), each port serving a different purpose. The admin port is used to access the solution in the container to infuse fluid from the container into the patient. The med port is used by a healthcare worker or a pharmacist to access the solution in the container to aspirate solution or to introduce medication and/or other substances (e.g., nutritional supplements, vitamins, etc.) into the container.

Both ports conventionally require the use of sharp objects to gain access to the solution in the container. The admin port is usually defined by a thermoplastic tube or chimney having a solid thermoplastic membrane, which membrane is disposed in the tube or chimney to prevent access to the solution in the container. A sharp spike (such as may conform to International Organization for Standardization Standard ISO 8536-4) is inserted into the tube or chimney, and advanced along the tube or chimney to pierce the membrane. The spike is attached to the administration set, and thereby establishes fluid communication between the container and the set. The med port conventionally includes a solid rubber septum that may be pierced using a needle, pointed cannula or other sharp instrument, such as a "reconstitution adapter."

The sharp, pointed instruments used to access the solution in the container via the admin or med ports represent an accidental puncture hazard to the healthcare worker or the pharmacist using the instrument, as well as a hazard to the patient, the equipment (e.g., the container), and others involved in the patient's healthcare. For example, the traditional unshrouded sharp spikes used to access the admin port can cause damage to container upon spiking. The spikes also present a puncture hazard to healthcare workers who handle the container as a waste container, especially where the container is a thin-film bag.

Moreover, there are other drawbacks to the conventional mechanisms used to access the solution in the container via conventional admin and med ports. For example, the use of the conventional sharp spike with an admin port can result in accidental disconnect, inadvertent touch contamination, and "no-flow" medication errors, which "no-flow" errors may result from the user failing to advance the spike far enough into the port in the absence of discrete feedback indicating complete connection. The ergonomic difficulty of connection/disconnection of the spike with the admin port may be aggravated where the tube or chimney that defines the admin port is flexible. Conventional admin ports do not reseal, requiring the user to invert the bag when removing the sharp spike to prevent leakage. On the med port side, the injection of medication using a syringe and needle requires non-trivial mechanical effort by the pharmacist or healthcare worker because of the small lumen size of the needle, when compared, for example, with the size of a conventional male luer.

As set forth in more detail below, the present disclosure sets forth an improved assembly embodying advantageous alternatives to the conventional devices discussed above.

SUMMARY OF THE INVENTION

According to an aspect of the present disclosure, a fluid container includes a receptacle for retaining a fluid, at least one conduit in communication with the receptacle, and the at least one conduit defined, at least in part, by a port assembly. The port assembly includes a housing with an opening and a bore therethrough, a slit septum disposed in the opening to control access through the opening, a base joined to the housing and having a membrane attached thereto, a perforator having a first end abutting the slit septum and a second end aligned with the membrane, and a resilient member disposed between the perforator and the base. The perforator has first and second lumens, the first lumen extending between the first and second ends of the perforator and the second lumen extending between a point between the first and second ends and the second end. The perforator also has a seal disposed about the first lumen at the first end of the perforator, and a valve associated with the second lumen to limit flow of fluid through the second lumen in the direction of the second end.

According to another aspect, port assembly to be used in a conduit of a fluid container is provided. The port assembly includes a housing with an opening and a bore therethrough, a slit septum disposed in the opening to control access through the opening, a base joined to the housing and having a membrane attached thereto, a perforator having a first end abutting the slit septum and a second end aligned with the membrane, and a resilient member disposed between the perforator and the base. The perforator has first and second lumens, the first lumen extending between the first and second ends of the perforator and the second lumen extending between a point between the first and second ends and the second end. The perforator also has a seal disposed about the first lumen at the first end of the perforator, and a valve associated with the second lumen to limit flow of fluid through the second lumen in the direction of the second end.

According to a further aspect, a port assembly to be used in a conduit of a fluid container is provided. The port assembly includes a housing with an opening and a bore therethrough, a slit septum disposed in the bore to control access through the opening, the slit septum including a sleeve having first and second ends and an inwardly-depending ring disposed at the second end of the sleeve, a base joined to the housing and having a membrane attached thereto, a perforator, and a resilient member disposed between the perforator and the base. The perforator has a first end abutting the slit septum, a second end aligned with the membrane, a passage between the first and second ends, and a bypass disposed at the first end of the perforator to permit fluid to flow between the passage and inbetween the inwardly-depending ring and an outer surface of the perforator.

Additional aspects of the disclosure are defined by the claims of this patent.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 17 is an enlarged cross-sectional view of a port assembly, similar to that illustrated in FIG. 9, in combination with a chimney of a gondola, such as is shown in FIGS. 15 and 16;

FIG. 18 is an enlarged cross-sectional view of another port assembly, similar to that illustrated in FIG. 9, in combination with a chimney of a gondola, such as is shown in FIGS. 15 and 16;

FIG. 19 is an enlarged cross-sectional view of a positive displacement variant of a port assembly, similar to that illustrated in FIG. 9;

FIG. 20 is an enlarged cross-sectional view of the port assembly of FIG. 19, with a male needleless connector partially inserted into the port assembly;

FIG. 21 is an enlarged cross-sectional view of the port assembly of FIG. 19, with a male needleless connector fully inserted into the port assembly;

FIG. 29 is a cross-sectional view of a port assembly according to a positive displacement variant with a luer tip in pre-insertion state;

FIG. 30 is a cross-sectional view of the port assembly of FIG. 29 immediately after insertion of the luer tip;

FIG. 31 is a cross-sectional view of the port assembly of FIG. 29 with fluid passing from the luer tip through the port assembly;

FIG. 32 is a cross-sectional view of the port assembly of FIG. 29 as the luer tip is removed from the port assembly;

FIG. 33 is a cross-sectional view of a port assembly according to a positive displacement variant similar to the port assembly of FIG. 29;

FIG. 34 is a cross-sectional view of a port assembly according to a multi-lumen, positive displacement variant with a luer tip in a pre-insertion state;

FIG. 35 is a cross-sectional view of the port assembly of FIG. 34 after insertion of the luer tip;

DETAILED DESCRIPTION OF VARIOUS EMBODIMENTS

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

Figure 1:
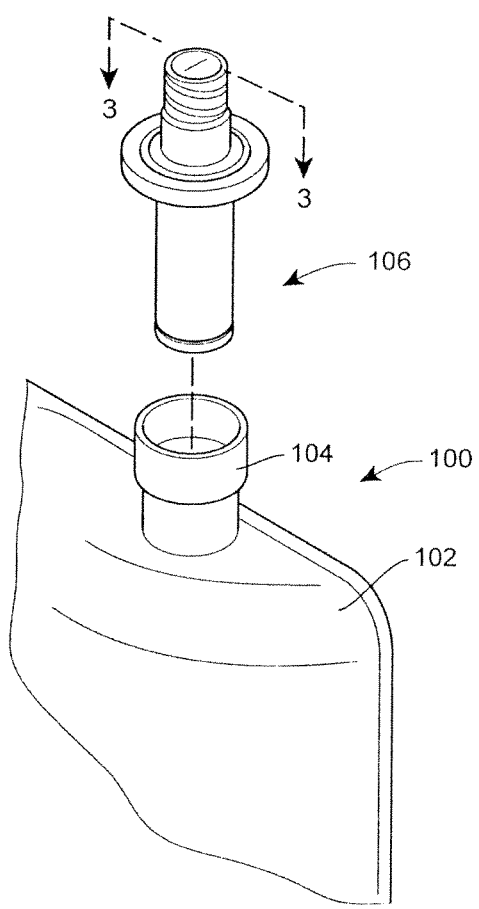
FIG. 1 is a fragmentary, perspective view of an embodiment of a fluid container with a needleless port assembly.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph FIG. 1 illustrates a fluid container 100 according to the present disclosure. The fluid container 100 includes a receptacle 102 for retaining a fluid, and at least one conduit 104 in communication with the receptacle 102. As illustrated, the receptacle 102 is a flexible bag formed using a polymer. However, the receptacle 102 could be a rigid-wall container, such as a glass bottle, or other container, such as a cartridge, unfilled flexible container, etc.

The fluid container of FIG. 1 is illustrated in combination with a first embodiment of a needleless port assembly, or port assembly, 106. The port assembly 106 is disposed in a port tube, as illustrated, to define the conduit 104. Although the port assembly 106 is shown separately from the port tube in the embodiment illustrated in FIG. 1, the port assembly 106 may include one or more structures that are integral with the remainder of the conduit 104, as illustrated and explained below.

Figure 2:
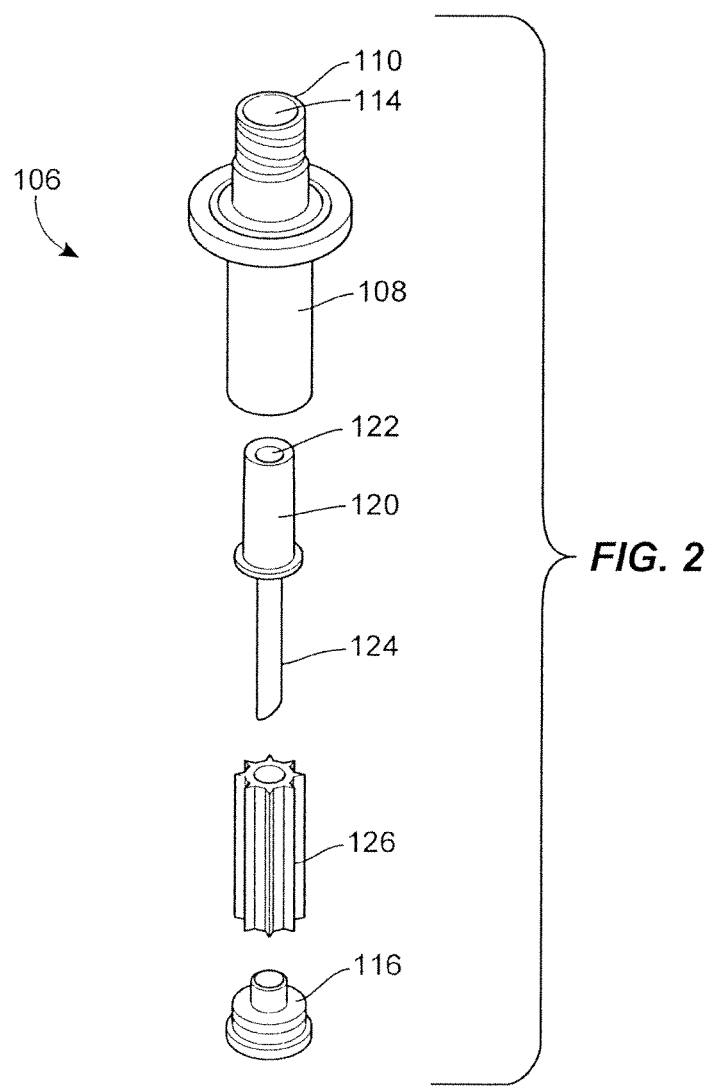
FIG. 2 is an exploded, perspective view of a port connector assembly as shown in FIG. 1.
Figure 3:
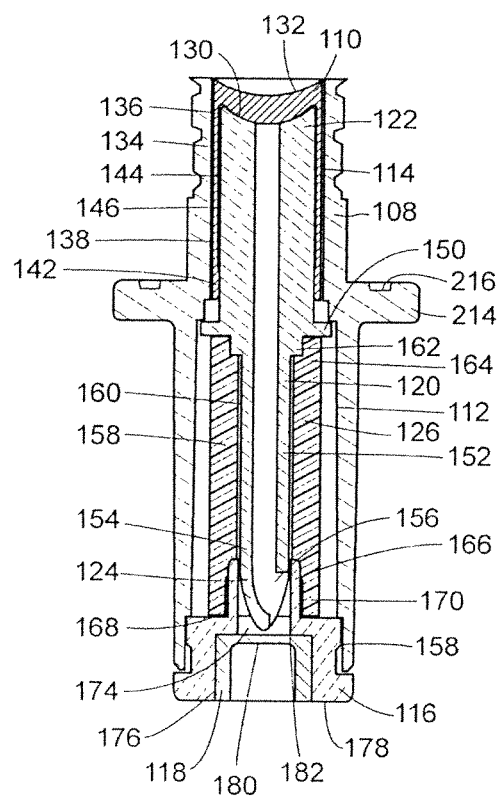
FIG. 3 is an enlarged, cross-sectional view of the port connector assembly of FIG. 1 taken about line 3-3.

In general terms, the port assembly 106 includes a housing 108 with an opening 110 and a bore 112 therethrough (see FIGS. 2 and 3). An overmolded slit septum 114 depends through the opening 110 and into the bore 112 to control access through the opening 110. A base 116 is joined to the housing 108 and has a membrane 118 attached thereto (see FIG. 3). The port assembly 106 also includes a perforator 120 having a first end 122 abutting the slit septum 114 and a second end 124 aligned with the membrane 118. A resilient member 126 is disposed between the perforator 120 and the base 116, biasing the perforator 120 from the membrane 118.

Figure 5:
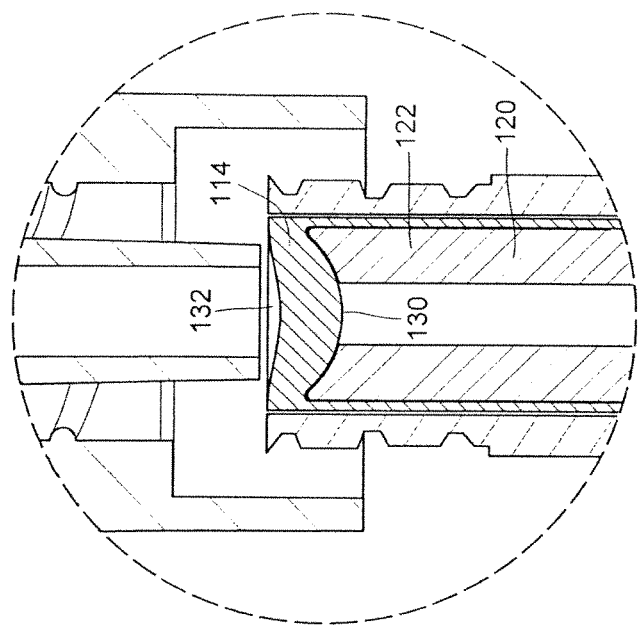
FIG. 5 is a fragmentary, enlarged, cross-sectional view of the port assembly with the perforator abutting the inwardly-concave septum.
Figure 4:
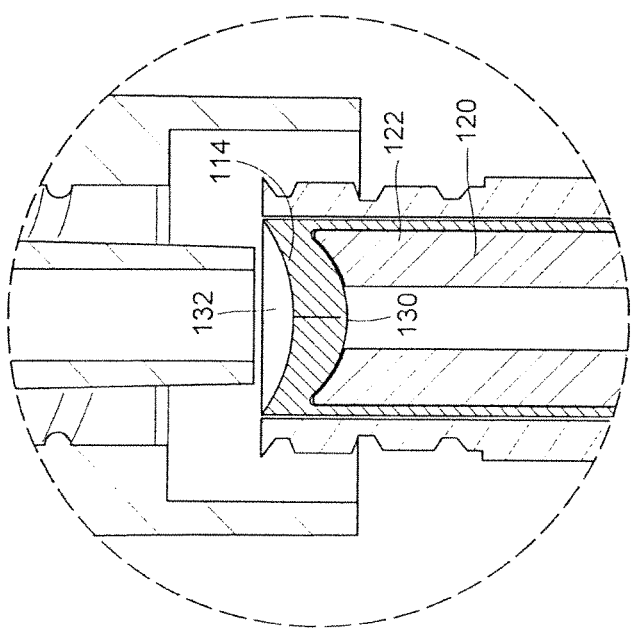
FIG. 4 is a fragmentary, enlarged, cross-sectional view of the port assembly with the perforator spaced from the inwardly-concave septum.

Referring now to FIG. 3 and starting at the opening 110, it will be recognized that the inner and outer surfaces 130, 132 of the slit septum 114 are concave prior to assembly, as illustrated in FIG. 4, and as assembled, as illustrated in FIG. 5. In particular, the inner surface 130 and the outer surface 132 have different radii of curvature, as illustrated. As is also illustrated, the radius of curvature, or simply "the curvature," of the outer surface 132 is greater than the curvature of the inner surface 130. It will be recognized that this is simply an embodiment according to the present disclosure, and that other septum shapes may be used as well, such as an embodiment wherein the inner and outer surfaces 130, 132 have similar radii of curvature, or where the differences in curvature are greater than are illustrated. The slit septum 114 shaped as illustrated may be referred to as an inwardly-concave overmolded slit septum. An inwardly-concave overmolded slit septum has certain advantages relative to conventional slit septums.

Certain conventional slit septums rely on a compression seal between a rigid housing (which may be made of metal, glass or plastic, for example) and the septum. In particular, a separate, individually-fabricated, oversized septum is disposed into an entrance of the housing, the outer diameter of the septum being greater than the inner diameter of the entrance of the housing. The septum may be attached to the housing mechanically (crimping, swaging, or threading, for example) or through the use of an adhesive, which attachment mechanisms may contribute to the compression seal. However, mechanical attachment is a challenge because of the dimensional constraints defined in ISO 594, and adhesive attachment creates manufacturing reliability challenges, especially for steam-sterilized applications.

Conventional overmolded septums remove the requirement for mechanical or adhesive attachment, but present other challenges. In particular, while it is desired for the overmolded part to have a flat surface, because a flat surface is believed to aid in the disinfection of the surface prior to use, the tension in the material because of post-mold shrinkage may result in slit opening, or separation, and subsequent leakage at low pressures. That is, when the septum is slit during the manufacturing process, the residual tensions in a flat overmolded septum cause the slit to open, creating leak channels. While flexing of the separation at relatively high pressures may force the slit closed, leaks may form at low pressures. Furthermore, the separation at the slit may extend into the septum, or through the septum in certain circumstances, and may provide a place for microbes to collect and grow, despite diligent efforts to clean and disinfect the septum surface.

It has been found that the inwardly-concave slit septum permits use of overmolding, thus eliminating the need for mechanical or adhesive attachment, while limiting the tension created when a flat overmolded septum is used. In particular, the inwardly-concave septum reduces the slit opening effect from post-mold shrinkage by allowing shrinkage of septum material in the axis of the septum rather than only perpendicular to the axis. The result is a septum with less stored strain energy, resulting in a lesser degree of separation when the septum is slit.

However, further improvements may be possible when the inwardly-concave overmolded slit septum is supported from within by a concave surface. Thus, as illustrated, the resilient member 126 biases the first end 122 of the perforator 120 into engagement with the slit septum 114. The first end 122 of the perforator 120 is concave, similar to the septum 114 and particularly the inner surface 130. The curvature of the first end 122 may be substantially similar to the curvature of the inner surface 130, as illustrated, so that the curvatures are mating. The engagement between the first end 122 and the inner surface 130 causes the flattening of the outer surface 132 from its initial shape (compare FIGS. 4 and 5). The distance of travel of the inner surface 130 between the state illustrated in FIG. 4 and that illustrated in FIG. 5 may be referred to as the assembly flexing distance. The flattening of the outer surface 132 need not result in a planar surface; some degree of curvature may remain. The flattening of the outer surface 132 of the septum 114 improves the ability of the septum 114 to be cleaned prior to use by swabbing or disinfecting according to conventional techniques.

Experimental results suggest that a septum deflection of 0.013 inches (0.33 mm) or better will prevent low-pressure (≦1 psi (0.0069 MPa)) leakage in inwardly-concave overmolded slit septums formed from silicone rubber. The experiments were conducted on slit septums made using silicone rubbers obtained from two different manufacturers and having a thickness of 0.080 inches (2 mm). In particular, the septums were made using rubbers having durometer readings of 30, 40 and 50. The septum displacements ranged from between 0.013 to 0.029 inches (0.33 to 0.74 mm), and no significant low-pressure leakage was observed. Consequently, it is believed that a deflection in excess of 0.013 inches (0.33 mm) should be suitable to prevent low-pressure leakage.

The cooperation of the perforator 120 and the septum 114 may have other effects, other than simply causing the flattening the outer surface 132. The flattening of the septum 114 also may concentrate forces on the slit, assisting in establishing a compression seal on the slit. It will be recognized, that excessive force applied to the septum 114 may actually result in spreading the septum, causing a separation to form along the slit, so there is a balance of forces involved. However, the cooperation of the perforator 120 and the septum 114 may result in a seal that is resistant to high or low pressure from fluid within in the container.

Returning then to FIG. 3 and continuing along the housing 180, the slit septum 114 includes a sleeve 134 having first and second ends 136, 138, as will be noted in FIG. 3. Further, the septum 114 includes an inwardly depending ring 142 disposed at the second end 138 of the sleeve 134. The inwardly depending ring 142 abuts an outer surface 144 of the perforator 120 to form the equivalent of an O-ring seal with the outer surface 144 to limit leakage of injected medication into the spaces outside the perforator 120. This seal is beneficial as the interface between a luer stem or tip and the first end 122 of the perforator 120 would not otherwise typically provide a sealing relationship and would add to the residual volume of the port assembly 106.

The perforator 120 has a flange 150 and a hollow tube or cannula 152 that depends from the flange 150 to the second end 124 of the perforator 120. According to the embodiment illustrated in FIGS. 1-8, the cannula 152 ends in a pointed profile 154. The resilient member 126 spaces the second end 124 of the perforator 120, and in particular the pointed profiled 154, from the membrane 118, and in part determines the size of the force required to move the second end 124 of the perforator 120 into contact with the membrane 118 to rupture the membrane 118 as a needleless connector is advanced into the slit septum 114. See FIGS. 6-8. The pointed profile 154 may have one or more apertures 156 through which fluid may pass when the perforator 120 penetrates the membrane 118; a single aperture is illustrated in the embodiment illustrated.

As is illustrated in FIG. 3, the resilient member 126 is defined by a flexible tube 158 with a passage 160 therethrough. The cannula 152 of the perforator 120 is received within the passage 160 in the flexible tube 158 that defines the resilient member 126. The resilient member 126 may have an outer shape that assists in permitting the resilient member 126 to flex without crushing; according to one such embodiment, the cross section of the resilient member 126 in a plane perpendicular to the plane of the page would appear as an eight-pointed star with a circular hole in the center. See FIG. 2. The resilient member 126 is also designed to limit potential residual volume around the cannula 152.

According to certain embodiments of the present disclosure, the resilient member 126 forms a liquid-tight, hermetic seal about the cannula 152 to limit leakage of medication into the space about the cannula 152. In particular, the flange 150 may have a stepped shoulder 162, the stepped shoulder 162 being disposed inside with a first end 164 of the resilient member 126. Furthermore, the base 116 may include a cylindrical collar 166 that defines a shoulder 168, collar 166 being disposed inside a second end 170 of the resilient member 126 abutting the shoulder 168. The resilient member 126 may have a smaller inner diameter than an outer diameter of the stepped shoulder 162 of the perforator 120 or the collar 166 of the base 116, and may expand to accommodate the stepped shoulder 162 and the collar 166 within the resilient member 126. As stated above, the seals thus formed limit leakage out of the space between the resilient member 126 and the cannula 152, which leakage may prevent medication from entering the container 100 and reduce the delivered dose.

The cylindrical collar 166 also defines a passage 174 in which the pointed profile 154 of the perforator 120 is received to align the pointed profile 154 with the membrane 118. As illustrated, the passage 174 is adjacent a recess 176 in a surface 178 of the base 116. The cup-shaped membrane 118 is formed in the recess 176, by heat sealing or a two-shot molding process, for example, so that a wall 180 of the membrane 118 spans an opening 182 defined between the passage 174 and the recess 176. In this fashion, the wall 180 of the membrane 118 is aligned with the pointed profile of the perforator 120 to facilitate the proper penetration of the membrane 118 by the perforator 120.

Figure 6:
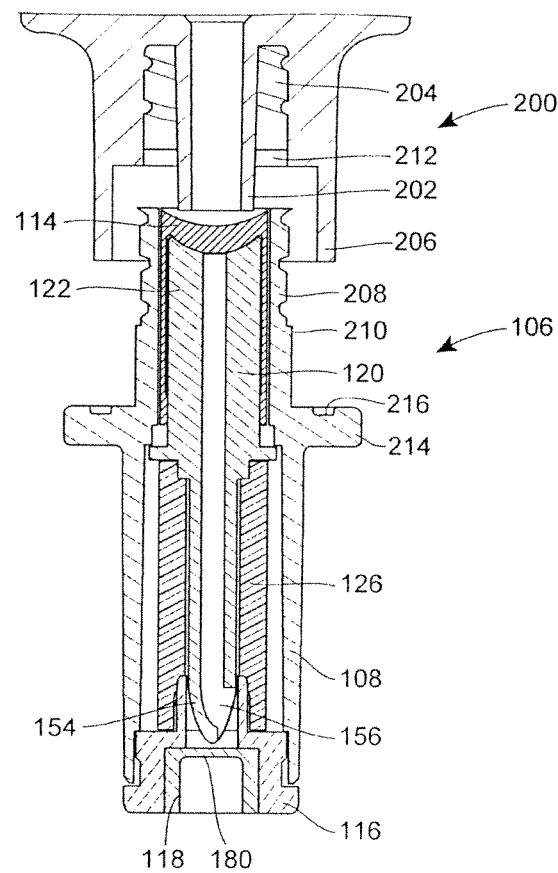
FIG. 6 is an enlarged, cross-sectional view of a male needleless connector in use with the port assembly of FIG. 1 in a preparatory state.
Figure 7:
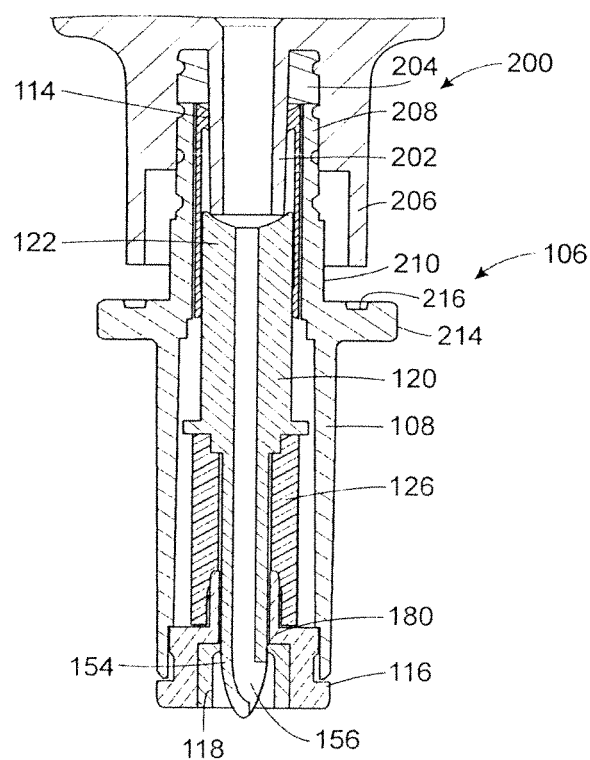
FIG. 7 is a combination of the male needleless connector and the port assembly in an inserted state, after rupture of the membrane but prior to full extension.
Figure 8:
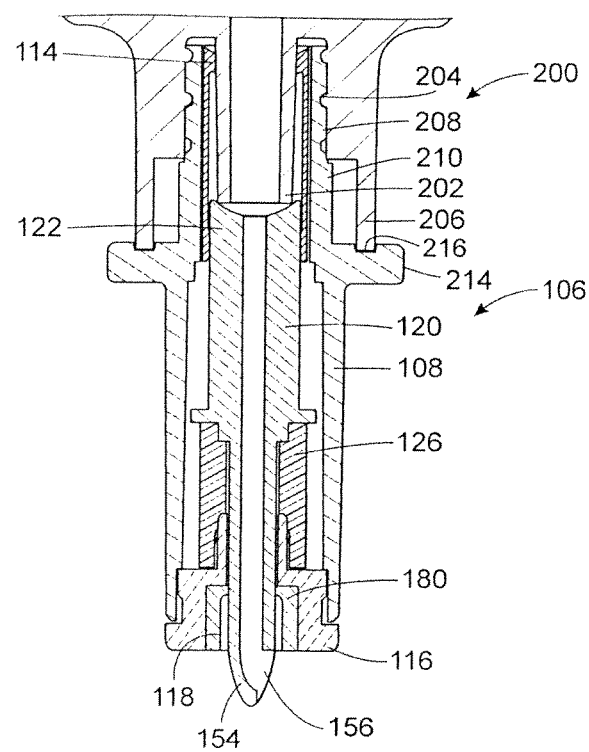
FIG. 8 is a combination of the male needleless connector and the port assembly in an inserted state, after rupture of the membrane with full extension.

The operation of the embodiment of the port assembly 106 is now discussed with reference to FIGS. 6-8. The port assembly 106 is illustrated in FIGS. 6-8 in combination with a male needleless connector 200, which cooperates with the port assembly 106 to move the perforator 120.

As illustrated, the connector 200 represents a non-conventional luer-type connector, which may be used with other I.V. administration sets, syringes, or other ancillary devices such as reconstitution adapters, as well as with the port assembly 106. However, it will be recognized that the port assembly 106 may be used with conventional luer-type devices, such as syringes or I.V. tubing connectors, having dimensions in accordance with International Organization for Standards Standard ISO 594. These non-conventional and conventional connectors may have a threaded region, such a connector being referred to as a "luer lock"; however, according to certain embodiments of the present disclosure, the connectors may lack a threaded region, such a connector being referred to as a "slip luer."

Returning then to FIGS. 6-8, the connector 200 has a luer stem or tip 202 that is surrounded by a threaded region 204. More particularly, an extended shroud or skirt 206 is disposed about the luer tip 202, the shroud 206 being attached, with the luer tip 202, to a common base at one end and depending further from the base than the luer tip 202 at the other, according to the illustrated embodiment. The shroud 206 has an inner surface on which the threaded region 204 is formed. The threaded region 204 of the connector 200 is intended to cooperate with threads 208 on an outer surface 210 of the housing 108. The penetration depth of the luer stem 202 is thus proportional to the amount of rotation applied to the connector 200.

As compared with conventional luer-type devices in accordance with ISO 594, the connector 200 is designed to provide increased penetration depth for the luer stem 202 into the port assembly 106. The increased penetration depth is intended to provide for increased exposure of the apertures 156 as the pointed profile 154 penetrates the membrane 118 and displaces the portion of the membrane 118 so penetrated (the "membrane flap"). Increased exposure of the apertures 156 may lead, in turn, to increased flow rate when using the connector 200 as illustrated in comparison with use of a conventional luer-type device in accordance with ISO 594.

In this regard, the connector 200 includes an unthreaded, or plain, region 212, which is best seen in FIG. 6. The unthreaded region 212 is defined between an end of the threaded region 204 and a shoulder formed in the inner surface of the shroud 206. The unthreaded region 212 causes the threaded region 204 to be recessed from the end of the connector 200. Because, as mentioned above, the penetration depth is otherwise proportional to the amount of rotation applied to the connector 200, the unthreaded region permits the end of the luer stem 202 to be disposed into the port assembly 106 prior to engagement of the threaded regions 204, 208 of the connector 200 and the port assembly 106. The distance may be, for example, the equivalent of a half turn to a full turn of the connector 200 relative to the port assembly 106. This arrangement avoids requiring the user to apply more rotation to achieve increased penetration, and may even be combined with a luer stem length in excess of that required by ISO 594 to provide even greater penetration.

It should also be noted that the connector 200 includes a shroud or skirt 206. This shroud 206 cooperates with a flange 214 arranged on the outer surface of the port assembly 106. The combination of the shroud 206 and the flange 214 provides a further, unique feature of the connector 200, which may be used in combination with the unthreaded region 212, or separately from that feature, to the advantage of the user.

In particular, in conventional luer-type connectors, the connector provides tactile feedback to the user regarding the progression of the connector on to the mating structure through gradual resistance to further tightening. The combination of the shroud 206 and the flange 214, however, provides a visual indication in combination with such tactile feedback. That is, when the threaded regions 204, 208 have fully engaged, the user is highlighted to this fact through the abutment of the shroud or skirt 206 and the flange 214.

According to certain embodiments, the flange 214 may include an annular groove 216, in which the shroud 206 is disposed as the threaded regions 204, 208 become fully engaged. The groove 216 may have a slight taper from an open end to a closed, or blind, end to improve the tactile feedback. The groove may also define a seal between the shroud 206 and the flange 214, which seal may further limit leakage from the combination of the connector 200 and the port assembly 106.

Further improvements in the sealing between the shroud 206 and the flange 214 may be provided by disposing a gasket between the shroud 206 and the flange 214. This gasket may be used with the groove 216, or may be used as a separate feature. The gasket may be made separately from the shroud 206 or the flange 214 and attached thereto, or the gasket may be formed on one of the facing surfaces of the shroud 206 and flange 214 through the use of a two-shot molding process, for example. Particularly, one or more apertures may be defined in the wall of the housing 108 so that the same material that is used to form the slit septum 114 may be permitted to flow through the housing 108 and over the flange 214 to define the gasket thereon.

Further, such gasket-defining material may enhance the friction between a rim of the shroud 206 and a surface of the flange 214 when the structures cooperate. The additional resistance provided may result in additional tactile feedback to limit further rotation. The frictional cooperation between shroud 206 and flange 214 may be further enhanced through snap ribs, slots or other structure disposed on one or both of the shroud 206 and the flange 214, which features may be used with the one or both of the groove 216 and gasket, or may be used independently.

It will also be recognized that the frictional cooperation of the shroud 206 and the flange 214 may also provide increased connection security, in that the additional resistance to rotation in the direction of further tightening also results in additional resistance to rotation in the direction of disengagement. Of course, if it is desired to limit or reduce the additional resistance caused by the frictional cooperation between the shroud 206 and the flange 214, then other structures may be used to the shroud 206 and the flange 214 to reduce friction between the structures.

It will be recognized that the use of the shroud 206 may provide other advantages. For example, the shroud 206 may limit the potential for touch contamination of the luer 202 of the connector 200. Further, the shroud 206 may aid in alignment upon connection, and to this end alignment ribs may be included inside the shroud 206; for example, four to eight ribs may be disposed within the shroud 206 to assist in alignment.

Figure 28:
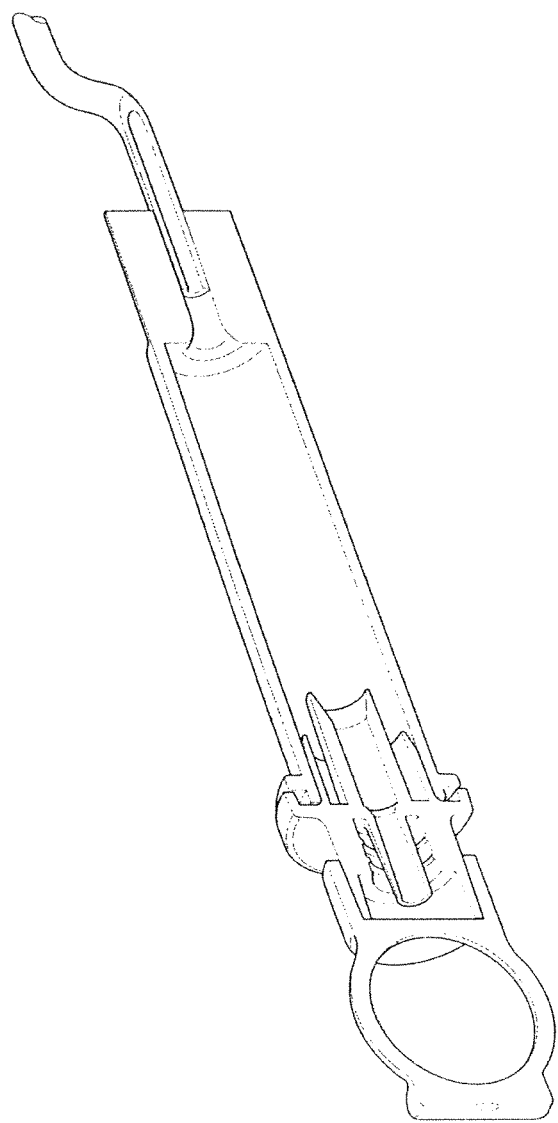
FIG. 28 is a cross-sectional view of a male needleless connector in combination with a connector for an administration set.

It is also possible to incorporate or to attach other features to the connector 200. For example, a flexible "drip chamber" may be attached to the connector 200 to connect the connector 200 to tubing of an I.V. administration set. Alternatively, as illustrated in FIG. 28, the connector 200 may be connected directly to the administration set.

As shown in the preparatory position in FIG. 6, the luer stem 202 is just coming into contact with the slit septum 114. At this point, the resilient member 126 is biasing the perforator 120, and in particular the pointed profile 154, away from the wall 180 of the membrane 118. The resilient member 126 will continue to bias the pointed profile 154 of the perforator 120 away from the wall 180 of the membrane as the luer stem 202 is advanced into the slit septum 114, the threads 208 of the housing 108 interacting with the threaded region 204 of the male connector 200.

Eventually, the force applied to the first end 122 of the perforator 120 causes the pointed profile 154 to rupture the wall 180 of the membrane 118, as shown in FIG. 7. The pointed profile 154 then proceeds to pass by the membrane 118 into the fluid container. As the threads 208 of the housing 108 continue to interact with the threaded region 204 of the male connector 200, more and more of the aperture 156 is exposed, without partial occlusion caused by the base 116 or part of the membrane 118, such as the membrane flap.

As shown in FIG. 8, the threads 208 of the housing 108 and the threaded region 204 of the male connector 200 have now cooperated to their maximum extent. The pointed profile 154 now depends past the membrane 118 and base 116, such that the aperture 156 is in fluid communication with the receptacle 102 without occlusion caused by the base 116. It will be recognized that as the when the luer stem 202 of the male connector 200 is withdrawn from the port assembly 106, the perforator 120, and thus the pointed profile 154 and associated aperture 156, will be withdrawn into the base 116, which will then again partially occlude the flow of fluids through the perforator 120.

Figure 9:
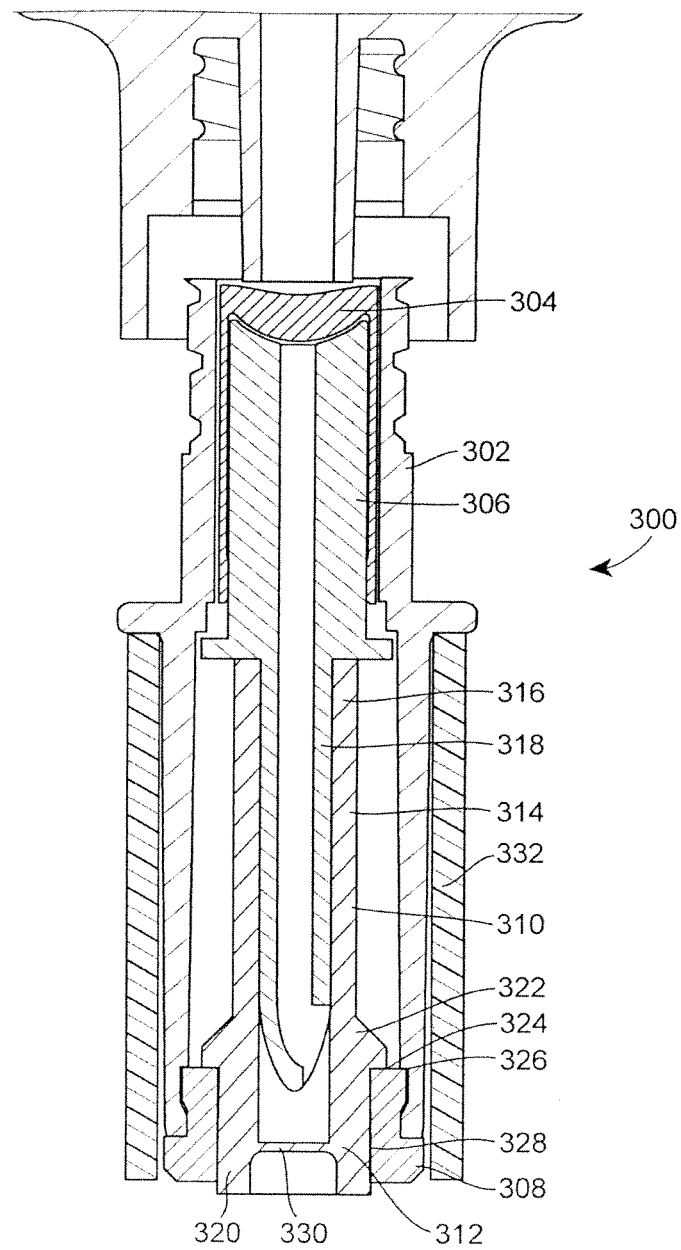
FIG. 9 is an enlarged, cross-sectional view of another port assembly.
Figure 10:
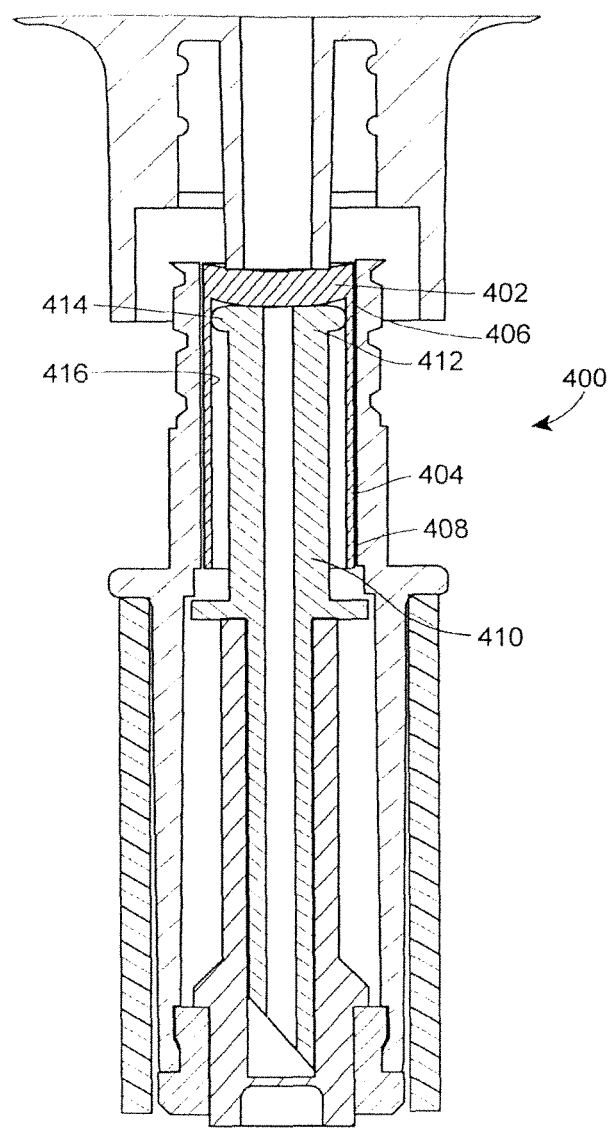
FIG. 10 is an enlarged, cross-sectional view of a further port assembly.
Figure 11:
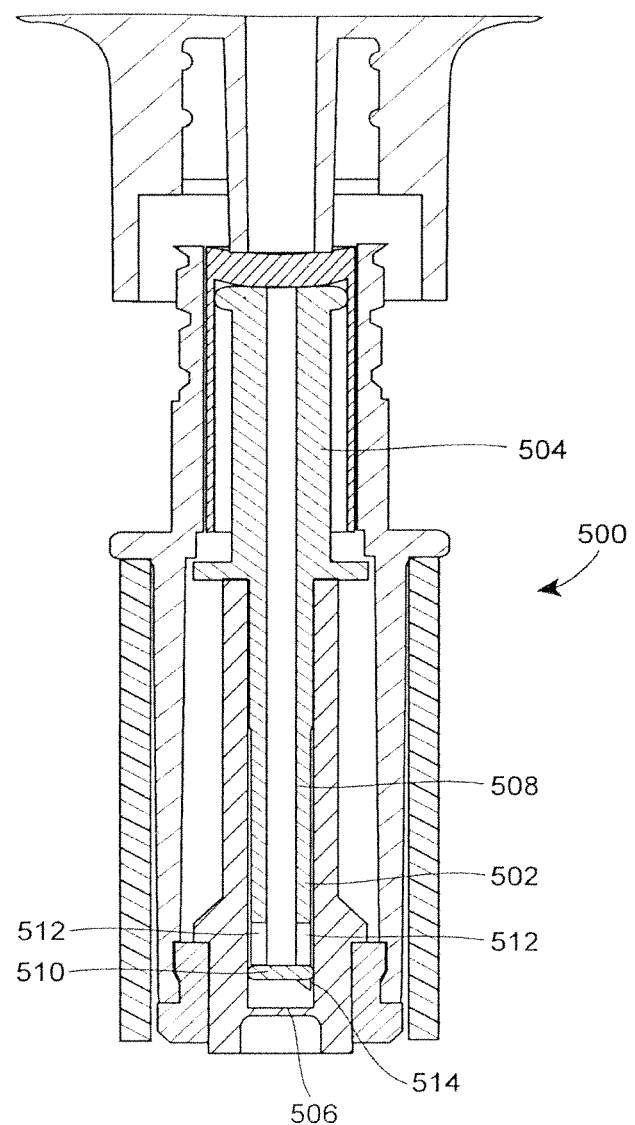
FIG. 11 is an enlarged, cross-sectional view of yet another port assembly.

The embodiment of FIGS. 1-8 is but a single embodiment of the port assembly according to the present disclosure. Other embodiments are illustrated in FIGS. 9-11. It will be recognized, however, that aspects of the embodiments illustrated in the FIGS. 9-11 may be used with the embodiment of FIGS. 1-8, and vice versa. Moreover, the elements of the various embodiments may be used in combination with each other. For example, the integrated resilient member and membrane illustrated in FIG. 9 may be used in combination with the variant in regard to the cooperation between the septum and perforator illustrated in FIG. 10, as will be recognized. Other variations are possible.

Starting then with the embodiment illustrated in FIG. 9, it will be recognized that the structure of the port assembly 300 is similar to that illustrated in FIGS. 1-8 as relates to the housing 302, the septum 304, and the perforator 306. However, the base 308, resilient member 310 and membrane 312 of the embodiment of FIG. 9 differs significantly from that of FIGS. 1-8. The resilient member 310 includes a flexible tube 314 with an open end 316 in which a cannula 318 of the perforator 306 is received, much like the embodiment illustrated in FIGS. 1-8. However, the resilient member 310 also includes a closed end 320. The closed end 320 is formed in the base 308, by a two-step molding process, for example, and defines the membrane 312.

In particular, the closed end 320 of the resilient member 310 includes a flange 322 that defines a shoulder 324. The shoulder 324 seats against a surface 326 of the base 308 to position the section of the flexible tube 314 that acts as the resilient member 310. However, the flexible tube 314 depends past the surface 326 of the base 308, and through a passage 328. A wall 330 depends across the tube 314 at an end 320 of the tube 314 within the passage 328, thereby defining the membrane 312. The tube 314 thus provides some of the features of the collar 166 in the embodiment illustrated in FIGS. 1-8, in that the tube 314 aligns the perforator 120 with the membrane 312, at the same time the wall 330 formed with the tube 314 defines the membrane 312. The assembly 300 may then be secured in place onto the I.V. container through connection to a flexible port tube 332, which is connected to the remainder of the container.

Another embodiment of a port assembly 400 is illustrated in FIG. 10. The differences in regard to the other embodiments primarily relate to the cooperation between the slit septum 402 and a first end 404 of a perforator 406, although it should be noted that the angled profile of the perforator 406 is also different from the pointed profile illustrated in FIGS. 1-9. An advantage of the angled profile of the perforator 406 is that is may provide maximum aperture exposure at limited penetration distances, in accordance with the bevel angles and the non-concentric or offset lumen of perforator 406.

As discussed above with reference to the embodiment illustrated in FIGS. 1-8, the slit septum 114 according to that embodiment has an inwardly directed ring 142 that cooperates with a surface 144 of the perforator 120 to seal the septum 114 and perforator 120 to limit infiltration into and out of the space between the surfaces 144, 146 of the perforator 120 and septum 114. According to the embodiment of FIG. 10, the slit septum 402 includes a sleeve 404 having first and second ends 406, 408. However, rather than the sleeve 404 having an inwardly depending ring that cooperates with the outer surface of the perforator to limit the passage of matter into the space between the sleeve and the outer surface of the perforator, the perforator 410 according to this embodiment includes a first end 412 with an outwardly-depending wiper 414. The outwardly-depending wiper 414 abuts an inner surface 416 of the sleeve 404, and forms a seal therebetween to prevent leakage.

The embodiment of FIG. 10 may have one or more advantages relative to the embodiment illustrated in FIGS. 1-8. For example, because the sealing surface depends outwardly from the perforator 410, rather than inwardly from the septum 402, the sleeve 404 may have a thicker wall thickness than that illustrated in FIGS. 1-8. The increased wall thickness may aid the overmolding of the septum 402. Furthermore, the removal of the ring from the sleeve further simplifies the overmolding process. Additionally, the removal of the ring limits or reduces the residual volume relative to the embodiment of FIGS. 1-8. Also, the outwardly-depending wiper 414 may provide positive displacement of liquid contents upon withdrawal of the associated connector, the importance of which is explained in greater detail below.

According to a further embodiment of a port assembly 500, illustrated in FIG. 11, the difference in regard to the other embodiments relates to the shape of the end 502 of the perforator 504 that punctures the membrane 506. In particular, the end 502 of the perforator 504 has a blunt profile, in contrast with the pointed profile 154 illustrated in the embodiments disclosed in FIGS. 1-9 or the angled profile illustrated in the embodiment disclosure in FIG. 10. While the perforator 504 includes a cannula 508, this cannula 508 ends not in an angled point, but in a plate 510 that lies in a plane perpendicular to the axis of the cannula 508. While the plate 510 may be equipped with a point 514 to assist the blunt profile of the first end 502 of the perforator 504, as is illustrated, the profile of the perforator 504 remains blunt. According to such an embodiment, the cannula 508 may include one or more apertures 512.

As illustrated, the plate 510 may have a periphery with an outer diameter greater than the inner diameter of the resilient member 126, and may thus form a liquid-tight seal. According to other embodiments, the plate 510 and the resilient member 126 need not form a liquid-tight seal. According to still other embodiments, the plate 510 and the resilient member 126 may form a liquid-tight seal, and this seal may permit the membrane 506 to be removed altogether. The further consequence of such an embodiment would be to position the plate 510 closer to the second end of the housing 108, further limiting or reducing residual volume. Other advantages of such an embodiment would be a reduction of the force or effort required, an increase in the flow rate for a limited connector penetration depth, caused by the fact that the apertures 512 do not need to depend past a membrane flap, and the creation of a vacuum in the perforator cannula, which may reduce aerosolizition when the luer stem clears the septum.

Figure 12:
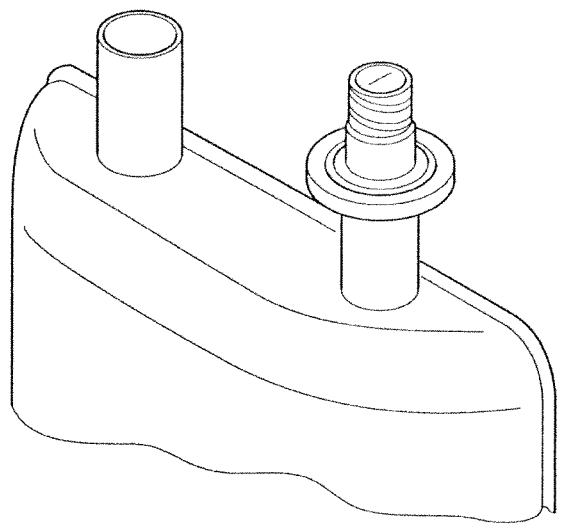
FIG. 12 is a perspective view of a two-port fluid container with a port assembly introduced into one port tube.
Figure 13:
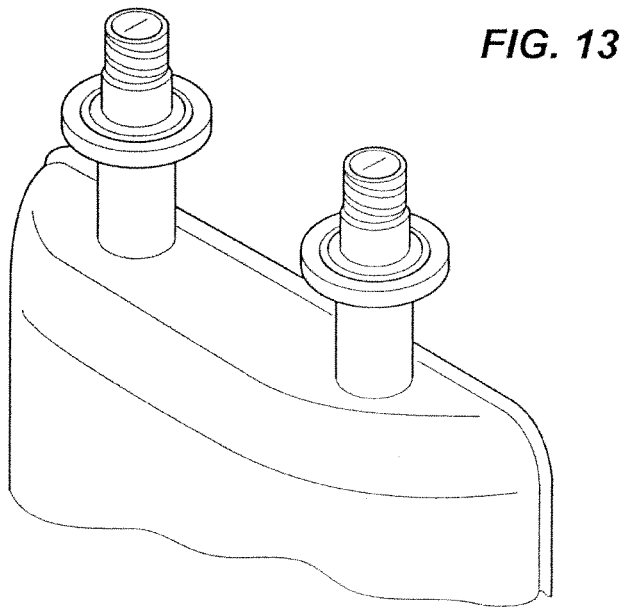
FIG. 13 is a perspective view of a two-port fluid container with a port assembly introduced into both port tubes.
Figure 14:
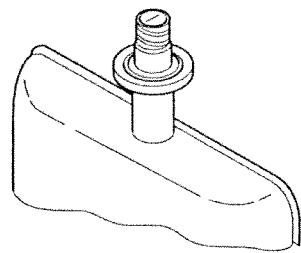
FIG. 14 is a perspective view of a one-port fluid container with a port assembly introduced into the port tube.
Figure 15:
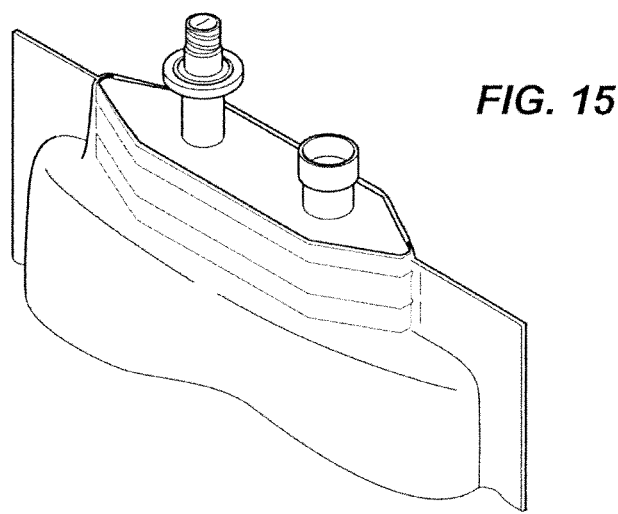
FIG. 15 is a perspective view of a two-port fluid container having a gondola with a port assembly introduced into one chimney.
Figure 16:
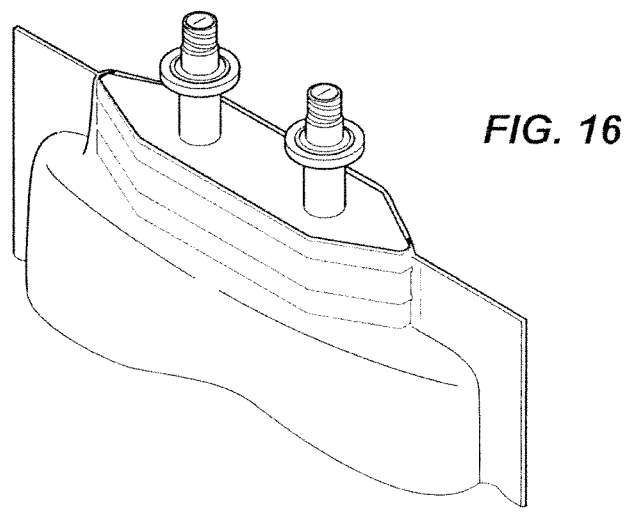
FIG. 16 is a perspective view of a two-port fluid container having a gondola with a port assembly introduced into both chimneys.

As illustrated in FIGS. 12-16, a needleless port assembly according to any of the embodiments described above may be incorporated into a fluid container according to any of a variety of configurations. FIGS. 12-14 illustrate embodiments wherein a fluid container includes a port tube, the port assembly disposed in the port tube to define the conduit. FIGS. 15 and 16 illustrate embodiments wherein a fluid container includes a gondola, the gondola including a chimney that is formed integrally with the base of the port assembly to define the conduit. It will be recognized that typically the port assemblies would have sterile port protectors or caps covering the ends; the caps have not been shown to facilitate visualization of the port assembly placement. As a further alternative, the port assembly may have a peelable foil seal disposed over the opening as a sterility protector.

It will be recognized that in a fluid container having two port tubes, at least one of the port tubes is used by a pharmacist to add medication or other materials to the fluids in the bag, and is referred to as the med port, while at least one of the other port tubes is used by the healthcare professionals to connect the fluid container to the line, and is referred to as the admin port. FIG. 12 illustrates an embodiment wherein the port assembly is utilized in the med port, and another mechanism, such as a conventional spike, is used in the admin port. FIG. 13 illustrates an embodiment wherein a port assembly according to the present disclosure is utilized in both the admin and the med ports. By contrast, FIG. 14 illustrates an embodiment wherein the port assembly is utilized in a single port embodiment.

Fluid containers utilizing gondolas have a similar convention relative to the designation of med and admin ports, the inclusion of the gondola coming about because of difficulties in joining the chimney material to the receptacle material. FIG. 15, like FIG. 12, illustrates an embodiment wherein the port assembly is utilized in the med port. FIG. 16, like FIG. 13, illustrates an embodiment wherein the port assembly is utilized in the admin and med ports. In particular, relative to the embodiment utilizing a gondola, the base may be formed integrally (i.e., as one piece) with the gondola, as discussed above.

According to an embodiment illustrated in FIG. 17, however, a port assembly 600, similar to those illustrated above, may be connected to a gondola without forming any part of the port assembly integrally (i.e., as one piece) with the gondola. In particular, the port assembly 600 includes a housing 602, a slit septum 604, a perforator 606, a base 608, a resilient member 610 and a membrane 612, all similar to the port assembly of FIG. 9. Specifically, the resilient member 610 and the membrane 612 are formed integrally with each other. That is, the resilient member 610 includes a flexible tube 614 with an open end 616, in which a cannula 618 of the perforator 606 is received, and a closed end 620. The closed end 620 defines the membrane 612. Furthermore, the resilient member 610 and the membrane 612 are formed with the base 608 using a two-step molding process, for example.

To connect the port assembly 600 to the gondola, the base 608 includes at least one lug or hook 622. As illustrated, the base 608 includes two hooks 622, which depend from the base 608 from an outer surface 624. These hooks 622 may cooperate with features of a chimney 630 to limit the separation of the base 608 from the chimney 630, thereby attaching the port assembly 600 to the chimney 630. In particular, the chimney has a flange 632 with a surface 634. Each hook 622 may have a surface 636 that cooperates with the surface 634 of the chimney flange 632 such that the port assembly 600 cannot move about its axis (rotation) or vertically (translation).

Moreover, the combination may include features to limit leakage between the port assembly 600 and the chimney 630. A gasket 640 may be formed through a two-step molding process on the flange 632, although it will be recognized that this gasket may alternatively be formed separately from the flange 632 and disposed in the chimney 630. As a further alternative, the gasket 640 may be formed on the base 608. The gasket 640 is disposed between the base 608 and the chimney flange 632, and in particular between opposing surfaces 624, 642 of the base 608 and chimney flange 632 so that the surfaces 624, 642 abut the gasket 640 as assembled. The gasket 640, in conjunction with the chimney 632, ensures the fluid-tightness of the assembly.

It will be recognized that variants to the embodiment illustrated in FIG. 17 are possible. For example, an alternative embodiment of a port assembly 650 is illustrated in FIG. 18. According to the port assembly 650, no gasket is disposed between opposing surfaces of a base 652 of the port assembly 650 and a flange 654 of a chimney 656 of the gondola. Instead, the base 652 of the port assembly 650 has a groove 660 formed in an outer surface 662 of the port assembly 650, and a sealing member 664 is disposed in the groove 660. The sealing member 664, which may be in the form of an O-ring, is disposed between the base 652 and an inner surface 666 of the chimney 656 to limit fluid leakage past the port assembly.

In regard to advantages, the use of the above-mentioned port assembly, according to any of the various embodiments described herein, as the med port for a container may provide one or more of the following advantages relative to conventional med ports. As an initial matter, the use of the port assembly as described herein eliminates the use of sharp instruments, such as needles and reconstitution adapters, as have been used with conventional med ports, thereby eliminating the hazard posed to the pharmacist and the equipment (e.g., the container). Additionally, because the lumen size of a luer is typically significantly larger than the lumen size of needles used with the conventional med ports, there may be a reduced force required to aspirate solution or to inject a substance into the container via the port assembly. Further, the port assemblies according to the present disclosure are expected to be significantly more durable relative to conventional med ports, given the quality of the reseal possible with a slit septum to a septum that may be repeatedly perforated in use.

Similarly, use of the port assembly, according to any of the various embodiments described above, as the admin port may provide one or more of the following advantages relative to conventional admin ports. Replacement of the conventional admin port with the port assemblies according to the present disclosure would eliminate use of the conventional sharp spike, thereby eliminating a potential puncture hazard to equipment, patients, and healthcare workers. Furthermore, given that the administration set may now be connected to the container through the threaded engagement of a male luer connector attached to the set to the port assembly as disclosed, accidental disconnects may be limited. Further, the threaded engagement of the luer connector to the port assembly according to the present disclosure may provide a discrete feedback to the healthcare worker of complete connection, limiting "no-flow" medication errors. Additionally, the port assemblies according to the present disclosure would limit the ergonomic difficulties in fitting the conventional spikes into flexible tubes or chimneys. Further, the port assemblies disclosed here reseal after disconnection of the connector, which may prevent leakage currently occurring after disconnection of a conventional sharp spike from a conventional admin port.

Further, it will also be recognized that the port assemblies according to the present disclosure facilitate use of a single port as admin port and med port. That is, convention admin ports did not have a resealable membrane, such that once the membrane was ruptured, leakage would occur. This presents an obstacle to use of conventional admin ports as med ports, which by the nature need to be resealable. Similarly, conventional med ports required a sharp, pointed instrument, such as a needle, to penetrate the septum. The flow rates possible through a needle are insufficient to permit connection of the administration set to the container in this fashion. However, because a male luer will provide flow rates sufficient for use of the port assembly as an admin port, the same luer-activated port assembly used first as a med port may later be used as an admin port as well.

It will also be recognized that certain of the embodiments of the port assembly discussed above address the interrelated issues of dose recovery and bolus infusion. As will be explained below, both issues arise from the amount of medication that remains in or about the med port after injection. If the med port is not used as the admin port, dose recovery may be the predominant issue, while bolus infusion may be addressed through the use of conventional injection and mixing techniques. On the other hand, if the med port is used as the admin port, bolus infusion may become the primary issue, with dose recovery being of lesser concern.

In a two-port container with separate med and admin ports, if the medication injected via the med port remains in or about the med port, then this fraction of the medication is unlikely to mix with the other fluids in the container when conventional mixing techniques are used. Failure to mix may decrease the likelihood that the medication in or about the med port will be delivered to the patient during infusion via the admin port. In fact, a "dose recovery fraction" may be calculated using the amount of medication infused from the container and the intended dose injected into the container.

In a container that has or uses only one port as both med port and admin port, very little medication will be remain in or about the med port during or after infusion because mixing with the fluids in the container is not required to transport the medication from the med port to the admin port. As a consequence, near-100% dose recovery may be achieved. However, the failure of medication in or about the med port to mix with the fluids in the container may have a different effect. Assuming that only conventional mixing steps are performed or and that the med port is not flushed after use, the medication in or about the port may define a bolus of concentrated medication that may be delivered to the patient when the port is used as the admin port. Unless the bolus is mixes or dilutes in the administration set, it may be possible for the bolus to be delivered to the patient in the early stage of infusion. Such a bolus may have an undesired, even adverse, effect in the patient The degree to which the medication remains in or about the med port may depend on features of the med port system (including the geometry and/or volume of the port and the length and/or position of the instrument used to inject medication into the port) as well as the techniques used (including the injection technique and the mixing technique). The port assemblies according to the present disclosure use an instrument in the form of, for example, a luer tip on a syringe. A conventional luer tip is typically much shorter than a needle, which may increase the potential for medication to be inadvertently left in or about the med port.

On the one hand, the dimensions of the structures of the port assemblies, as well as the seals formed between these structures as described in greater detail above, may be used to limit the residual volume of the assemblies, thereby limiting reductions in the dose recovery fraction or increases in the potential for bolus infusion. However, a tradeoff remains between minimizing residual volume, thereby maximizing dose recovery or minimizing bolus infusion risk, and ensuring adequate flow rate through the single lumen perforator illustrated above. Consequently, it may be necessary to consider additional features.

The embodiments discussed above may additionally include one or more features that address the issues of dose recovery and bolus infusion, even when a conventional luer tip is used. For example, the embodiments illustrated in FIGS. 1-8 and FIG. 9, the pointed tip of the perforator projects well beyond the membrane so as to maximize the potential for delivery of the medication or other substance injected therethrough into the container where it will become mixed with the other fluids in the container. In the embodiment illustrated in FIG. 10, the offset or non-concentric perforator lumen may allows greater lumen exposure at a limited axial penetration depth, again so as to maximize the potential delivery of medication injected therethrough, while the wiper may provide positive displacement of the contents upon withdrawal of the associated connector, which positive displacement may increase dose recovery and reduce potential for bolus infusion. FIG. 11 may also work to increase dose recovery and reduce potential for bolus infusion by limiting the amount of residual volume in the port assembly through the presence of the plate 510.

However, any of the embodiments discussed above may be combined with still further features that operate to increase dose recovery and reduce the potential for bolus recovery. The embodiments in FIGS. 19-27 illustrated such further features that may be used to combat reduced dose recovery and/or increased potential for bolus infusion. Specifically, the embodiments of the port assembly illustrated in FIGS. 19-24 address features for creating positive displacement, so as to automatically flush the port assembly after injection. The embodiment of the port assembly illustrated in FIGS. 25-27 includes a multi-lumen perforator, with different lumens used when the port assembly is used either as a med port or an admin port. It is believed that these additional features may further improve dose recovery or reduce the potential for bolus infusion.

Referring first to FIGS. 19-22, a port assembly 700 is illustrated therein. Similar to the other port assemblies disclosed herein, the port assembly 700 includes a housing 702, a slit septum 704, a base 706, a perforator 708, a resilient member 710, and a membrane 712. The slit septum 704 is overmolded on the housing 702, and operates to control passage through the port assembly 700. The housing 702 is attached to the base 706 with the perforator 708 biased against the septum 704 and away from the membrane 712 by the resilient member 710. Similar to the embodiment illustrated in FIGS. 9, 17, and 18, the resilient member 710 and the membrane 712 are molded as a single piece with the base 706 using a two-shot molding process, for example.

Figure 22:
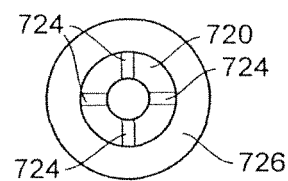
FIG. 22 is an enlarged end view of a perforator used in the port assembly according to FIG. 19.

The port assembly 700 differs from the port assemblies previously discussed in relation to the shape and structure of the perforator 708. The perforator 708 has a first end 720, which abuts the septum 704 in the standby state illustrated in FIG. 19, and a second end 722, which is pointed and is spaced from the membrane 712 in the standby state. As best seen in FIG. 22, the first end 720 of the perforator 708 includes a plurality of passages defined by grooves 724 disposed about the circumference of the first end 720; while four grooves 724 are illustrated in FIG. 22, a lesser or a greater number of grooves may be used in any particular embodiment. In between the first end 720 and the second end 722 is a flange 726. A flexible, elastomeric gasket 728 is disposed on the flange 726; the gasket 728 may be formed separately and fitted onto the flange 726, or the gasket 728 may be formed on the flange 726, through a two-step molding process, for example.

The port assembly 700 also differs from certain of the port assemblies previously discussed in relation to the shape and structure of the slit septum 704. The septum 704 includes a sleeve 730 having a first end 732, a second end 734, and an inner surface 736. Unlike certain port assemblies discussed above, the second end 734 of the sleeve 730 does not have a structure formed thereon to abut and seal against an outer surface 738 of the perforator 708. Instead, the inner surface 736 may be spaced between the first end 732 and the second end 734 of the sleeve 730 from the outer surface 738 of the perforator 708. The spacing may be constant between the first end 732 and the second end 734 of the sleeve 730, or the spacing may be larger in certain regions, while smaller in other regions. In fact, the inner surface 736 and the outer surface 738 may abut over certain regions; however, a fluid path should be maintained between the first end and the second end of the sleeve 730.

The perforator 708 cooperates with the septum 704, as well as the housing 702, to provide a positive displacement according to the following fashion.

As an instrument, for example a luer tip 750, is passed through the septum 704 and abuts the perforator 708, the perforator 708 is advanced along the housing 702 in the direction of the membrane 712. Eventually, the perforator 708 is advances so that the second, pointed end 722 of the perforator 708 punctures the membrane 712, as illustrated in FIG. 20. As a consequence, fluid may now flow, for example, through the luer tip 750 into the perforator 708, and from the perforator 708 into a container 752 associated with the port assembly 700.

However, before the fluid is injected into the container 752 via the luer tip 750, fluid may be drawn from the container 752. In particular, as the perforator 708 is advanced, a space 754 opens between the outer surface 738 of the perforator 708 and an inner surface 756 of the housing 702. This opening space 754 is believed to create a vacuum, which pulls fluid into the space 754 to fill it. While some material may be pulled from the luer tip 750, it is believed that the fluid may be mainly drawn from the container 752, which is typically a thin-walled flexible bag, providing little resistance to the movement of the fluid in contrast to the rigid-walled syringe associated with the luer tip 750.

Assuming then that the fluid is flowing from the container 752, the fluid would pass through the grooves 724 formed in the first end 720 of the perforator 708 and the path(s) formed between the surfaces 736, 738 of the septum 704 and the perforator 708 into the space 754. The fluid in the space 754 would not flow past the flange 726 of the perforator 708 because of the cooperation of the gasket 728 and the inner surface 756 of the housing 702, the gasket 728 abutting the inner surface 756 to define a seal therebetween. Further movement, as illustrated in FIG. 21, causes the second end 722 of the perforator 708 to advance into the container 752, at which time force may be applied to inject medication or other material into the container through the luer tip 750. It is believed that the medication or other material mainly would bypass the space 754 because the space 754 is already filled with fluid from the container 752.

As the luer tip 750 is withdrawn, the movement of the perforator 708 reverses direction, passing from the fully extended state illustrated in FIG. 21 to the standby state illustrated in FIG. 19. The movement of the flange 726 and the sealing provided between the gasket 728 and the inner surface 756 of the housing 702 causes the fluid in the space 754 (originally from the container 752) to flow through the passage(s) between the surfaces 736, 738 toward the grooves 724, along the perforator 708, and into the container 752. As a consequence, any medication in or about the port assembly 700 will experience an automatic flush as the luer tip 750 is withdrawn, which is believed to reduce the amount of medication in or about the port assembly 700. The reduction in medication in or about the port assembly 700 is believed to increase the dose recovery for the port assembly, or to reduce the risk of bolus infusion.

Figure 23:
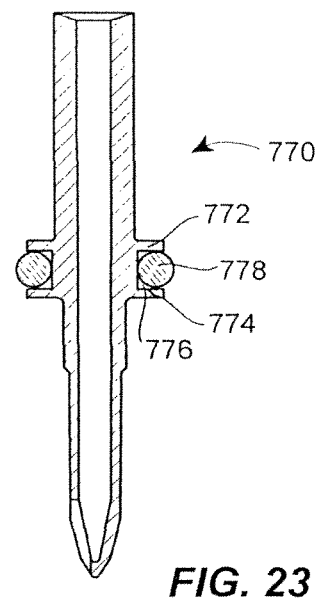
FIG. 23 is a cross-sectional view of another perforator for use in the port assembly according to FIG. 19.

It will be recognized that the embodiment in FIGS. 19-22 is amenable to variation. For example, a perforator 770 is illustrated in FIG. 23, which perforator 770 may be used with the port assembly 700. The perforator 770 differs from the perforator 708 as to the structure responsible for sealing the space 754 defined between the perforator and the housing. Rather than including a flange with a gasket disposed thereon, the perforator 770 includes a pair of flanges 772, 774 that define a slot or groove 776 therebetween. A sealing member 778, such as an O-ring, may be disposed in the slot 776, and may cooperate with an inner surface of the port assembly housing to limit fluid flow from the space defined between the perforator 770 and the housing.

Other changes may also be made to the perforator. For example, instead of using grooves formed in the first end of the perforator to define the passages, ribs may be formed on the first end of the perforator to define passages therebetween. According to either such embodiment, the end of the perforator is spaced from the luer tip such that sealing does not occur, permitting fluid flow.

Figure 24:
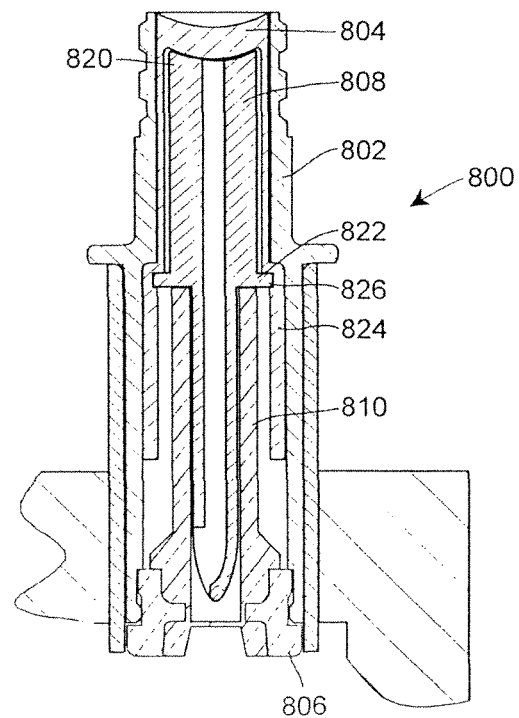
FIG. 24 is a cross-sectional view of a positive displacement variant of a port assembly, similar to that illustrated in FIG. 19.

A further variation is illustrated in FIG. 24. According to this embodiment, a port assembly 800 includes a housing 802, a slit septum 804, a base 806 and a perforator 808 biased between the housing 802 and the base 806 by a resilient member 810. The perforator 808, like the perforator 708, may have a plurality of grooves formed in a first end 820. Also, like the perforator 708, the perforator 808 may have a flange 822. However, the flange 822 does not have a sealing member associated therewith, such as perforators 708, 770 illustrated in FIGS. 19-23. Instead, the septum 804 has a sleeve 824 that depends further into the housing 802 than in the embodiments illustrated in FIGS. 19-22. The sleeve 824 is made of a resilient material, and cooperates with an edge 826 of the flange 822 to form a seal therebetween. The seal formed between the cooperation of the edge 826 of the flange 822 and the sleeve 824 limits leakage of fluid from a space defined between the perforator 808 and the housing 802, to provide the positive displacement similar to that discussed above relative to FIGS. 19-21.

Figure 26:
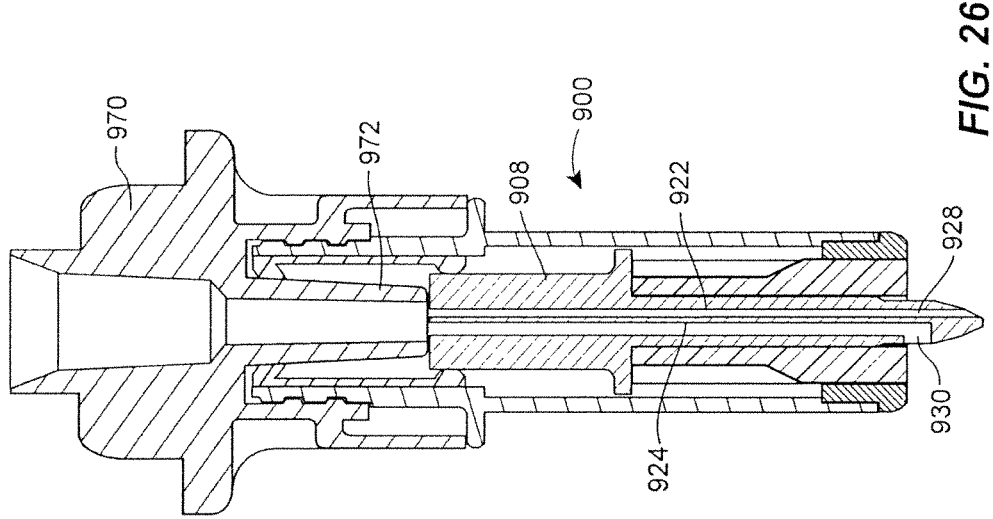
FIG. 26 is a cross-sectional view of the port assembly according to FIG. 25 in an admin port state.
Figure 25:
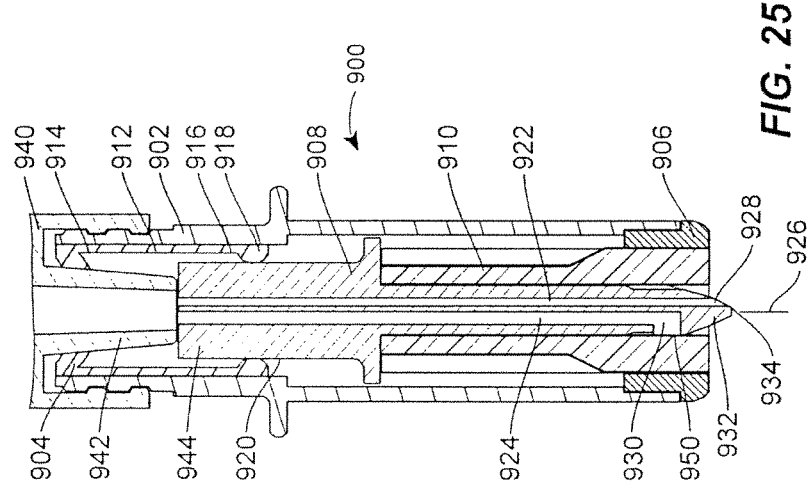
FIG. 25 is a cross-sectional view of a port assembly according to a multi-lumen variant, similar to that illustrated in FIG. 9, in an med port state.
Figure 27:
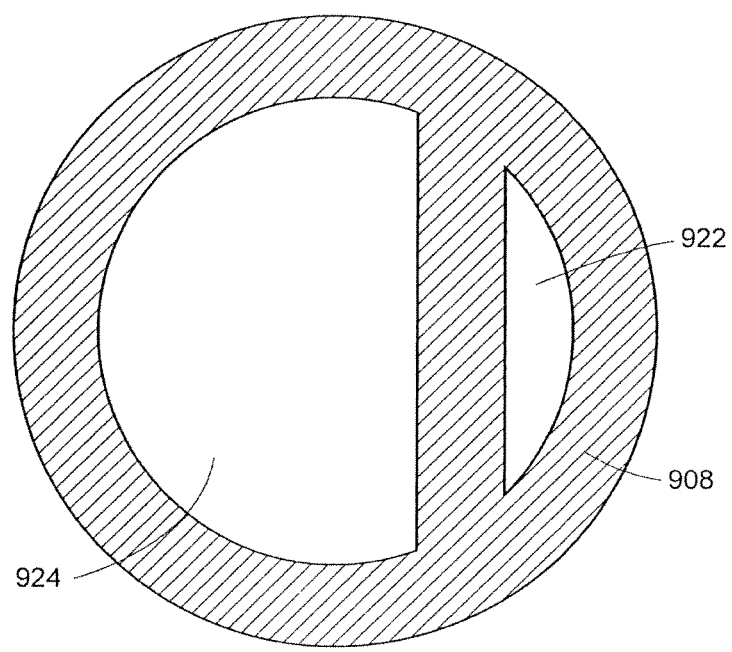
FIG. 27 is an enlarged cross-sectional view of a multi-lumen perforator used in the embodiment of a port assembly illustrated in FIGS. 25 and 26.

FIGS. 25-27 provide an alternative port assembly 900 that addresses the issues of dose recovery and bolus infusion in a different manner than the embodiments illustrated in FIGS. 19-24, which rely in part on positive displacement as discussed above. The port assembly 900 relies instead on a multi-lumen perforator instead of the single lumen perforator described above.

Referring then first to FIG. 25, it will be recognized that the port assembly 900 includes a housing 902, a slit septum 904, a base 906, a perforator 908, and a resilient member 910. Although not shown in FIGS. 25 and 26, it would be recognized that the resilient member 910 and the membrane would be formed as a single piece with the base 906 using a two-shot molding process, for example, similar to many of the other port assemblies described herein. The septum 904 includes a sleeve 912 having first and second ends 914, 916. Further, the septum 904 includes an inwardly depending ring 918 disposed at the second end 916 of the sleeve 912. The inwardly depending ring 918 abuts an outer surface 920 of the perforator 908 to form the equivalent of an O-ring seal with the outer surface 920 to limit leakage of injected medication into the spaces outside the perforator 908. In this regard as well, the port assembly 900 is similar to other port assemblies described above.

The perforator 908 is different than all of the perforators described heretofore in that the perforator 908 includes more than one lumen. Specifically, the perforator 908 includes a first lumen 922 and a second lumen 924. Both lumens 922, 924 are offset from a longitudinal axis 926 of the perforator 908. Moreover, both lumens 922, 924 have at least one aperture 928, 930 formed in a first end 932 of the perforator 908. As illustrated in FIG. 27, the first lumen 922 has a smaller cross-sectional area in a plane orthogonal to the axis 926 than the second lumen 924. Further, the aperture 928 associated with the first lumen 922 is disposed closer to an apex 934 of the end 932 than the aperture 930 associated with the second lumen 924, and the aperture 928 is aligned parallel to the axis 926, while the aperture 930 is disposed orthogonal to the axis 926.

The first and second lumens 922, 924, and in particular the apertures 928, 930 associated with the first and second lumens 922, 924, cooperate with the structure that defines the resilient member 910 and the membrane to maximize dose recovery and minimize bolus infusion as follows.

In a first operational state, as illustrated in FIG. 25, a first luer lock 940 is combined with the port assembly 900, the first luer lock 940 having dimensions in accordance with International Organization for Standards Standard ISO 594. The first luer lock 940 has a luer tip 942 that abuts a second end 944 of the perforator 908 to cause the perforator 908 to perforate the membrane and provide access to an associated container. With the membrane ruptured and the perforator 908 advanced into the container, the aperture 928 associated with the lumen 922 is exposed and fluid may flow through the lumen 922. However, the aperture 930 remains covered by an internal surface 950 of the resilient member 910/membrane structure. Consequently, it is believed that fluid from a syringe associated with the luer tip 942 will flow into the lumen 922, but not into the lumen 924, with the fluid taking the path of least resistance and/or the air trapped in the lumen 924 being unable to escape.

In a second operational state, as illustrated in FIG. 26, another luer lock 970 is combined with the port assembly 900, the luer lock 970 having a structure in accordance with the connector 200 illustrated in FIGS. 6-8, for example. The luer lock 970 has a luer tip 972, which luer tip 972, when combined with the port assembly 900, causes the perforator 908 to advance further into the container 946 than the luer tip 942 associated with the luer lock 940, given that the luer tip 972 is longer than that specified by ISO 594. According to this state, both apertures 928, 930 are exposed, permitting fluid to flow from the luer tip 972 through either lumen 922 or lumen 924. This is advantageously provides a larger cross-sectional area, collectively, for fluid flow in the second operation state than the first operational state.

By having two operational states wherein different lumens or combinations of lumens are available for fluid flow, dose recovery or bolus infusion may be controlled. In the first operational state, which may correspond to an operational state wherein medication is injected into the container 946, a smaller cross-sectional lumen 922 is available for fluid communication between an instrument, such as the luer lock 940, and the container 946. As a consequence, the amount of medication retained in the lumen 922 may be minimized by controlling the size of the lumen 922. By contrast, in the second operational state, which may correspond to an operational state wherein fluid is infused to the patient, a larger collective cross-sectional area passage is available. As a consequence, the amount of medication retained in the lumen 922 may even be diluted to some extent as the fluid passes through both lumens 922, 924 and into the luer tip 972. By varying the cross-sectional areas of the lumens 922, 924, as well as sizes of the apertures 928, 930, the considerations of dose recovery and bolus infusion may be balanced against adequate fluid flow.

It will be recognized that the multi-lumen embodiment of FIGS. 25 and 26 limits the potential for use of the luer lock 940 in place of the luer lock 970 when connecting an administration set to the container associated with the port assembly 900. If a luer lock 940 is used to connect an administration set to the container associated with the port assembly 900, it is likely that (i) a decreased flow rate relative to a desired flow rate will be observed and/or (ii) an upstream occlusion alarm associated with an IV pump may be triggered because only the lumen 922 is open. In either eventuality, it is believed that the luer lock 940 will then be replaced with the luer lock 970, which will provide adequate flow rate while addressing bolus effect and dose recovery.

It will be further recognized that a further embodiment may be envisioned that features the positive displacement of the port assembly of FIGS. 19-22, for example, with the multi-lumen perforator of the port assembly of FIGS. 25 and 26, such that the smaller lumen 922 is flushed as well. Given the relatively smaller volume in the lumen 922 of the perforator 908, the size of the space required to flush the lumen 922 need not be as large as is required for the single lumen perforators disclosed above. Alternatively, for a space similar to those disclosed above relative to the single lumen perforator, a larger volume of fluid may be displaced through the lumen 922 relative to the volume of the lumen 922.

Other modifications and variants of the port assembly 900 and the associated luer locks 940, 970 may be possible. For example, the luer lock 970 may be shaped so as to close off the lumen 922 at the same time as uncovering the aperture 930, thereby opening the lumen 924. In particular, the luer tip 972 of the luer lock 970 may have a structure that fits over or into the end of the lumen 922 closest to the luer tip 972. According to one embodiment, the inner diameter of the luer tip 972 may be sized so as to be smaller than the inner diameter of the luer tip 942 of luer lock 940, such that the rim of the luer tip 972 closes off the lumen 922. Alternatively, a projection may be formed on the luer tip 972 that closes off the lumen 922 when the luer lock 970 is engaged with the port assembly 900. The port assembly 900 and/or the luer lock 970 may include ribs or slots to ensure proper alignment of the luer lock 970 and the port assembly 900 in the engaged position. One result of the variant port assembly 900/luer lock 970 combination would be to limit the passage of the contents of the lumen 922 into the administration set, thereby further limiting the bolus effect, although potentially with some attendant loss of dose recovery.

Still further embodiments of a port assembly according to the present disclosure, including a slit septum and perforator, are illustrated in the embodiments of FIGS. 29-45. The embodiments of FIGS. 29-33 illustrate embodiments of a port assembly including positive displacement having a single lumen that extends between the ends of the perforator, but using air as the working fluid. The embodiments of FIGS. 34-45 illustrate embodiments of a port assembly including positive displacement and a multi-lumen perforator, thereby reinforcing how elements of the various embodiments discussed separately above may be combined according to still other embodiments.

Referring first to FIG. 29, the port assembly 1000 includes a housing 1002 with an opening 1004 and a bore 1006 therethrough. The opening 1004 is disposed at a first end 1008 of the housing 1002. An overmolded slit septum 1010 is disposed in the opening 1004 to control access through the opening 1004, and depends into the bore 1006. The cross-section of the bore 1006 may narrow slightly at the opening 1004 to define a rim 1012 with a shoulder 1014, against which the slit septum 1010 is disposed. The slit septum 1010 shaped as illustrated may be referred to as an inwardly-concave overmolded slit septum, as has been discussed in detail above.

The slit septum 1010 may be molded as a single structure (i.e., integrally) with a sleeve 1016 having first and second ends 1018, 1020. The sleeve 1016 has an inner surface 1022, and an inwardly depending ring 1024 disposed at the second end 1020 of the sleeve 1016. The structure and function of the ring 1024 will be discussed in detail below.

A base 1030 is joined to the housing 1002 at the opposite end 1032 of the housing 1002 from the opening 1004, and has a membrane 1034 attached thereto by molding the membrane 1034 thereon. As illustrated, a resilient member 1036 is formed as a single structure with the membrane 1034, and depends along the bore 1006 from the end 1032 of the housing 1002 in the direction of the end 1008. As will be recognized from the embodiments illustrated above, the resilient member 1036 may also be formed separately from the membrane 1034, such that the only the membrane 1034 is molded on the base 1030. The resilient member 1036 has an internal bore 1038 with a first and second ends 1040, 1042. The resilient member 1036 may have one or more grooves on or in an external surface 1044 to appear star-shaped in cross-section, such as the embodiment illustrated in FIG. 2.

The port assembly 1000 also includes a perforator 1050 having a first end 1052 abutting the slit septum 1010 and a second end 1054 aligned with the membrane 1034. As noted above, the first end 1052 of the perforator 1050 may have a surface 1056 that has a curvature similar to that of a surface 1058 of the slit septum 1010. The surface 1056 is held abutting against the surface 1058 according to the biasing provided by the resilient member 1036, the perforator 1050 being received within the bore 1038 of the resilient member 1036. To limit separation and provide a fluid-tight seal between the perforator 1050 and the resilient member 1036, the cross-section of the region of the perforator 1050 that mates with the first end 1040 of the bore 1038 of the resilient member 1036 may be slightly larger than the cross-section of the bore 1038 at this point.

Similar to the embodiment illustrated in FIG. 22, the first end 1052 of the perforator 1050 may have central lumen 1060 and a plurality of passages 1062, defined by grooves or channels, disposed about the circumference of the first end 1052. The passages 1062 are provided to permit passage of fluids between the lumen 1060 to provide the positive displacement referred to above. While four passages 1062 may be used as illustrated in FIG. 22, other numbers of passages may be used instead.

The perforator 1050 also includes one or more flanges 1064 disposed at or near the midsection of the perforator 1050, and a hollow tube or cannula 1066 that depends from the flanges 1064 to the second end 1054 of the perforator 1050. The flanges 1064 may have a gasket 1068 that is overmolded onto the flanges 1064, the gasket 1068 having an outwardly depending ring 1070 that abuts an internal surface 1072 of the bore 1006 of the housing 1002 to provide a fluid-tight seal therebetween. As will be recognized from the description of the operation of the port assembly 1000 below, this fluid-tight seal should limit the passage of both gases and liquids across the seal. The cannula 1066 ends in a pointed profile 1074, with at least one aperture 1076 formed therein.

Having thus described the structure of the port assembly 1000, the operation of the port assembly 1000 is now discussed with reference to FIGS. 29-32. In particular, the operation of the port assembly 1000 will be discussed in conjunction with the insertion and removal of a luer tip 1080. While the luer tip 1080 is formed as part of a luer lock, with mating threads of the housing 1002 and the luer lock cooperating to secure the luer tip 1080 to the port assembly 1000, the luer tip 1080 could just as easily be a slip luer instead.

As illustrated in FIG. 30, the luer tip 1080 is inserted into the port assembly 1000 and passed through the slit septum 1010, causing the slit septum 1010 to deflect. The luer tip 1080 abuts the first end 1052 of the perforator 1050, advancing the perforator 1050 in the direction of the membrane 1034 against the biasing of the resilient member 1036. The pointed profile 1074 of the perforator 1050 punctures the membrane 1034 and passes into the membrane 1034, but as illustrated the aperture 1076 has not yet passed through the membrane 1034.

At this point, a fluid path exists between the perforator 1050 and a space (or reservoir) 1090 that opens between the perforator 1050 and the inner surface 1072 of the housing 1002. The opening space 1090 is believed to create a vacuum, which pulls fluid into the space 1090 to fill it. Because the membrane 1034 has not yet been punctured to the point to permit fluid to pass through the membrane 1034 into the aperture 1076, fluid is not drawn from outside the port assembly 1000. Further, while some material may be pulled through the luer tip 1080, it is believed that the fluid will mainly be drawn from the bore 1038 of the resilient member 1036, which is filled with air at the time of manufacture.

It is presently believed that the volume of fluid within the space 1090 should be greater than a 1:1 ratio relative to the volume of the lumen 1060 to ensure adequate flushing of the lumen 1060. For example, it is believed that ratios of 3:1 or better for the volume within the space 1090 relative to the volume of the lumen 1060 should be attained. Of course, even higher ratios are believed to provide even better flushing results, and one may attempt to maximize ratio for a given configuration. For example, computational fluid dynamics indicates that an 8:1 ratio will leave a projected drug residue of approximately 0.013 percent in the lumen 1060 after withdrawal of the luer tip.

In maximizing the ratio, the cross-section of the lumen 1060 may be reduced to reduce the volume of the lumen relative to the volume of the space 1090, and thereby increase the ratio. However, it will be recognized that attempt to maximize the volume ration by reducing the cross-section of the lumen 1060 should be balanced with the need to limit flow resistance within the lumen 1060 caused by a reduction in cross-section. Flow resistance is relevant not only because the lumen 1060 may be used when injecting medication and other fluids through the port assembly 1000, but also because fluid may be aspirated from the container through the port assembly 1000 as well. For example, according to an embodiment of the present disclosure, the lumen 1060 may have a cross-sectional area that is double the cross-sectional area of an 18-gauge needle.

The air from the bore 1038 passes into the aperture 1076, into the lumen 1060, and through the passages 1062. The air would then pass between the first end 1052 of the perforator 1050 and the sleeve 1016. As illustrated, the ring 1024 is spaced from the first end 1052 of the perforator 1050, so that fluid may pass around the ring 1024 and into the space 1090. In addition or the in alternative, the first end 1052 of the perforator 1050 may have grooves or channels formed therein to facilitate fluid flow around the perforator 1050. The flow of fluid in the space 1090 past the flanges 1064 should be limited because of the cooperation of the gasket 1068 and the inner surface 1072 of the housing 1002.

Further movement, as illustrated in FIG. 31, causes the second end 1054 of the perforator 1050 to advance past the membrane 1034, at which time force may be applied to inject medication or other material into the container through the luer tip 1080. By this time, the first end 1052 of the perforator 1050 has come in contact with the ring 1024, such that the space 1090 has been sealed off. The medication or other material thus will bypass the space 1090. To facilitate this sealing, the first end 1052 of the perforator 1050 may include a head 1092 of larger cross-section, permitting a more positive seal to be formed between the perforator 1050 and the ring 1024.

As the luer tip 1080 is withdrawn, as illustrated in FIG. 32, the movement of the perforator 1050 reverses direction, passing from a fully extended state illustrated in FIG. 31 to a standby state illustrated in FIG. 29. The movement of the flanges 1064 and the sealing provided between the gasket 1068 and the inner surface 1072 of the housing 1002 causes the air in the space 1090 to flow along the flow path described above, and into the lumen 1060. As a consequence, any medication in or about the port assembly 1000 will experience an automatic flush as the luer tip 1050 is withdrawn, which is believed to reduce the amount of medication in the lumen 1060 and in or about the port assembly 1000. The reduction in medication in or about the port assembly 1000 is believed to increase the dose recovery for the port assembly, or to reduce the risk of bolus infusion.

A port assembly 1100 according to a variant of the port assembly 1000 is illustrated in FIG. 33. The differences between the port assembly 1000 and the port assembly 1100 are located at the first end of the perforator. Given the similarity of the two embodiments, similar structures have been numbered similarly with the inclusion of a prime for the embodiment illustrated in FIG. 33.

While the first end 1052 of the perforator 1050 included a plurality of passages 1064 formed in the surface 1056, the perforator 1050' lacks such passages 1064. Instead, the perforator 1050' includes one or more passages 1102 formed along a side surface 1104 of the head 1092' of the perforator 1050' facing the sleeve 1016'. These passages 1102 have a first end 1106 in fluid communication with the lumen 1060' of the perforator 1050', and a second end 1108 in fluid communication outside the perforator 1050'.

As a consequence, the surface 1056' may more closely mate with the inner surface 1058' of the slit septum 1010', without concern for discontinuities or sharp edges that may occur during manufacturing of the passages 1064 present in the perforator 1050. However, air is still permitted to pass through the lumen 1060' into the passages 1102 as the luer tip is inserted into the port assembly 1100, or to pass through the passages 1102 into the lumen 1060' as the luer tip is removed from the port assembly 1100. As such, the operation of the port assembly 1100 is very similar to the operation of the port assembly 1000, while the placement of the passages 1102 may permit a smoother surface 1056' to be manufactured.

As mentioned above, the embodiments of FIGS. 34-45 are similar to the embodiments of FIGS. 29-33 in that a flushing is provided. However, to better control the passage of the fluid used to flush the main lumen of the perforator, one or more secondary lumens may be incorporated, in association with one or more valves, into the perforator. As will be recognized from the Figures, the secondary lumens may be disposed inside or on the outside of the perforator, and may be combined with one-way or multi-state valves.

Referring first to a port assembly 1120 illustrated in FIGS. 34 and 35, there are similarities between the overall structure of the port assembly 1120 and the port assemblies 1000, 1100. Similar to the embodiments above, the port assembly 1120 includes a housing 1122 with an opening 1124 and a bore 1126 therethrough. The opening 1124 is disposed at a first end 1128 of the housing 1022. An inwardly-concave overmolded slit septum 1130 is disposed in the opening 1124 to control access through the opening 1124. The slit septum 1130 may be molded as a single structure (i.e., integrally) with a sleeve 1132 having first and second ends 1134, 1136 and an inner surface 1138. Unlike the embodiments of FIGS. 29-33, there is no ring disposed at the second end 1136 of the sleeve 1132.

A base 1140 is joined to the housing 1122 at the opposite end 1142 of the housing 1122 from the opening 1124, and has a membrane 1144 molded thereon. A resilient member 1146 is formed as a single structure with the membrane 1144, and depends along the bore 1126 from the end 1142 of the housing 1122 in the direction of the end 1128. The resilient member 1146 has an internal bore 1148 with a first and second ends 1150, 1152.

The port assembly 1100 also includes a perforator 1160 having a first end 1162 abutting the slit septum 1130 and a second end 1164 aligned with the membrane 1144. As noted above, the first end 1162 of the perforator 1160 may have a surface 1166 that has a curvature similar to that of a surface 1168 of the slit septum 1130. The surface 1166 is held abutting against the surface 1168 according to the biasing provided by the resilient member 1146, the perforator 1160 being received within the bore 1148 of the resilient member 1146. To limit separation and provide a fluid-tight seal between the perforator 1160 and the resilient member 1146, the cross-section of the region of the perforator 1160 that mates with the first end 1150 of the bore 1148 of the resilient member 1146 may be slightly larger than the cross-section of the bore 1148 at this point.

Unlike the embodiment of FIG. 22 or FIGS. 29-32, the perforator 1160 does not have passages at the first end 1162. Quite the contrary, the perforator 1160 has a seal 1170 formed on the first end 1162. In particular, the perforator 1160 has a main, or principal, lumen 1172 having a first end 1174 about which the seal 1170 is disposed. The seal 1170 is intended to form a fluid-tight seal with a luer tip 1180 when the luer tip 1180 is inserted into the port assembly 1100 through the slit septum 1130 and abuts the first end 1162 of the perforator 1160. It will be recognized that this seal could alternatively be formed (by molding, for example) on the end of the luer tip 1180.

The perforator 1160 includes one or more flanges 1190 and a hollow tube or cannula 1192 that depends from the flanges 1190 to the second end 1164 of the perforator 1160. The flanges 1190 may have a gasket 1194 that is overmolded onto the flanges 1190, the gasket 1194 having an outwardly depending ring 1196 that abuts an internal surface 1198 of the bore 1126 of the housing 1122 to provide a fluid-tight seal therebetween. The cannula 1192 ends in a pointed profile 1200, with at least one aperture 1202 formed therein that is in fluid communication with a second end 1204 of the main lumen 1172.

The perforator 1160 includes one or more secondary lumens 1210 formed at least partially on an outer surface 1212 of the perforator 1160. As illustrated, the perforator 1160 illustrated in FIGS. 34 and 35 includes a single secondary lumen 1210. The secondary lumen 1210 depends along the perforator 1160 between the second end 1164 of the perforator 1160 and the one or more flanges 1190 depending outwardly from the perforator 1160. In particular, the secondary lumen 1210 has a first section 1214 that is parallel to a longitudinal axis of the perforator (and hence parallel to the main lumen 1172) and a second section 1216 that is at an angle to the first section 1214 with an opening 1218; as illustrated, the first and second sections 1214, 1216 are orthogonal to each other, although this should not be construed as limiting the lumen 1210 to only such a configuration.

A valve 1220 is disposed over the opening 1218. The valve 1220 may comprise a flap of material that is molded over the opening 1218 at the same time that the gasket 1194 is molded to the perforator 1160. The flap may be separated from the remainder of the material during a post-molding operation, so as to define the valve 1220. The valve 1220 is a one-way valve, permitting fluid to flow through the secondary lumen 1210 in the direction of the first end 1128 of the housing 1122 and limiting flow of fluid through the secondary lumen 1210 in the direction of the second end 1142 of the housing 1122.

The operation of the port assembly 1120 may now be discussed with a comparison between FIGS. 34 and 35. With the luer tip 1180 inserted into the first end 1128 of the housing 1122 and passed through the slit septum 1130, the luer tip 1180 abuts the first end 1162 of the perforator 1160. Because of the presence of the seal 1170 disposed on the first end 1162 of the perforator 1160, the passage of fluid from the luer tip 1180 through other than the main lumen 1172 is limited. Force may be applied to the perforator 1160 via the luer tip 1180 to advance the perforator 1160 in the direction of the membrane 1144.

As the perforator 1160 is advanced in the direction of the second end 1142 of the housing 1122, a space 1230 opens between the perforator 1160 and the inner surface 1198 of the housing 1122, as illustrated in FIG. 35. The space 1230 is believed to create a vacuum, which pulls fluid into the space 1230. Because the luer tip 1180 is sealed so as to limit fluid passage through other than the main lumen 1172, it is believed that the fluid drawn into the space 1230 will come from the container associated with the port assembly 1100, through the secondary lumen 1210 and past the valve 1220. Because the fluid received in the space 1230 has not yet mixed with the injectable fluid from the luer tip 1180, the flushing of the main lumen 1172 and the adjacent volume within the container will be enhanced (i.e., the injectable fluid cleared from the lumen 1172 will be further diluted) when the luer tip 1180 is withdrawn and the fluid is expelled from the space 1230. It will also be recognized that the absence of the grooves or channels present in other embodiments and the presence of the seal 1170 will limit the number of irregularities on the surface 1166 that may otherwise result from manufacturing and may cause damage to the slit septum 1130.

As the luer tip 1180 is withdrawn, transitioning between a fully extended state illustrated in FIG. 35 and a standby state illustrated in FIG. 34, the perforator 1160 reverses direction. However, because of the friction between the perforator 1160 and the housing 1122, the luer tip 1180 will separate from the first end 1162 of the perforator 1160 despite the biasing force provided by the resilient member 1146. As a consequence, a gap develops between the luer tip 1180 and the first end of the perforator 1160.

As the gap begins to open between the luer tip 1180 and the first end of the perforator 1160, the fluid is urged out of the space 1230 by the movement of the flanges 1190 and the sealing provided between the gasket 1194 and the inner surface 1198 of the housing 1122. This fluid passes through the gap between the luer tip 1180 and the first end of the perforator 1160 and into the lumen 1172. As a consequence, any medication in or about the port assembly 1120 will experience an automatic flush as the luer tip 1180 is withdrawn, leading to a reduction in the amount of medication in the lumen 1172 and in or about the port assembly 1120.

FIGS. 36-45 illustrate a number of variants that would have a structure similar to the port assembly 1120 illustrated in FIGS. 34 and 35, differing only as to the structure of the perforator. In particular, the differences relate to the shape, manufacture and operation of the valve associated with the secondary lumen. These variant port assemblies would operate similar to the port assembly 1120, as will be discussed in detail relative to the embodiment of FIGS. 36-39, and will be recognized by extension to the further variants of perforator illustrated in FIGS. 40-42 and 43-45.

Figure 36:
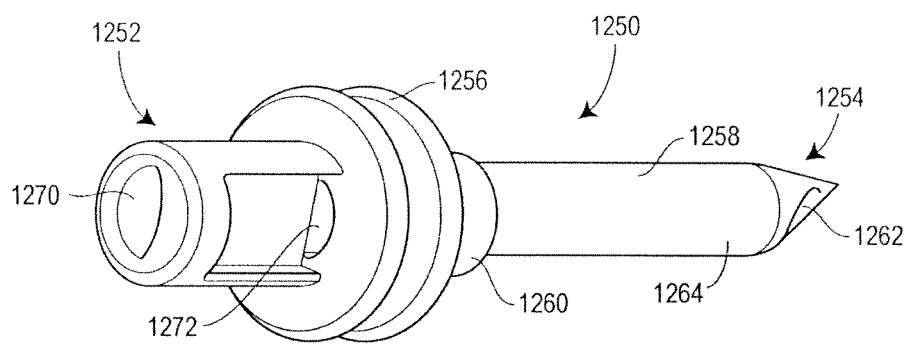
FIG. 36 is a perspective view of a perforator for use in a port assembly, prior to a second step of a two-shot molding process.
Figure 37:
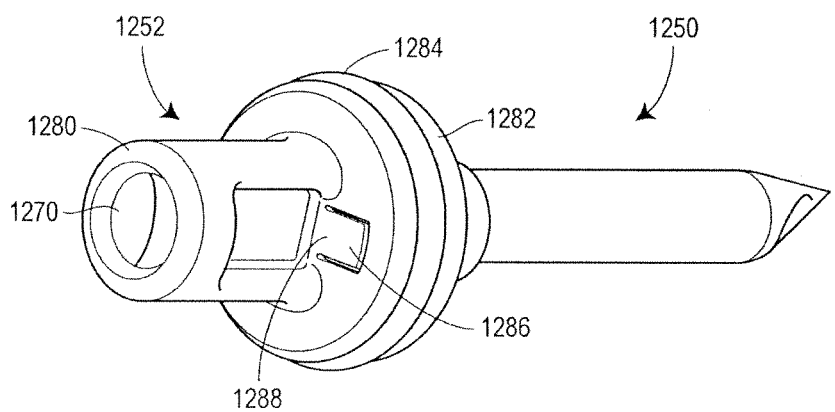
FIG. 37 is a perspective view of the perforator of FIG. 36 after the second step of the two-shot molding process to define a valve thereon.

FIGS. 36 and 37 illustrate a perforator 1250, before and after the second step of a two-shot molding process. As seen in FIG. 36, the perforator 1250 has a first end 1252 and a second end 1254. Disposed between the first and second ends 1252, 1254 are a pair of flanges 1256, although a single flange could have been included instead. A cannula 1258 is connected to the flanges 1256 at a first end 1260 and has pointed profile 1262 as a second end 1264.

Figure 39:
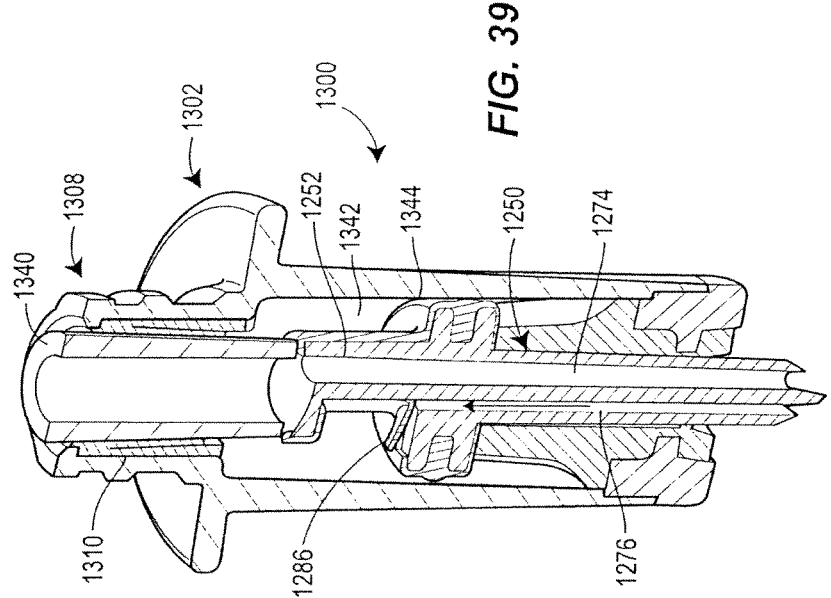
FIG. 39 is a cross-sectional view of the port assembly of FIG. 38 after insertion of the luer tip with the valve open.
Figure 38:
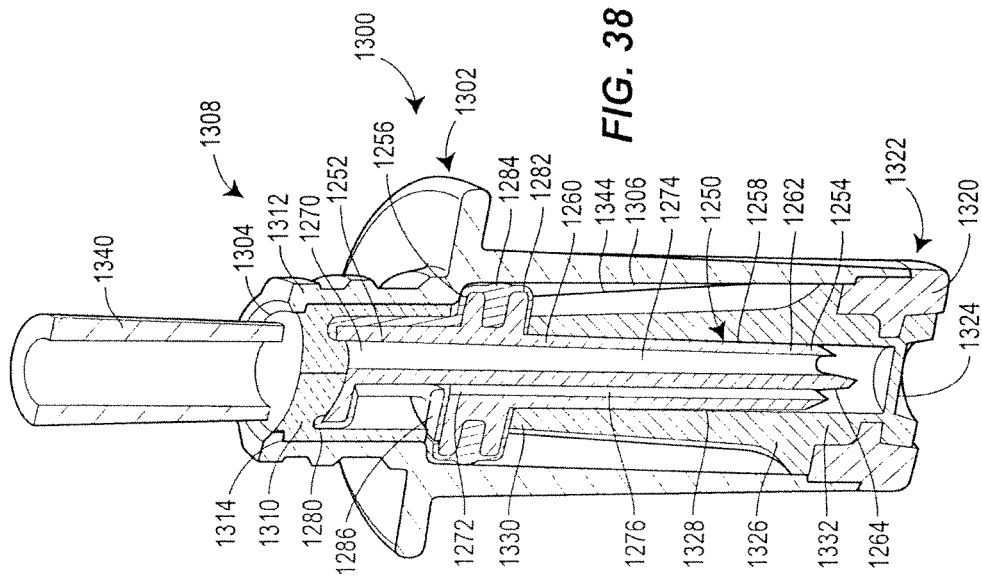
FIG. 38 is a cross-sectional view of a port assembly according to a multi-lumen, positive displacement variant incorporating the perforator of FIG. 36, with a luer tip in a pre-insertion state.

Two apertures 1270, 1272 are formed at or near the first end 1252 of the perforator 1250. The two apertures 1270, 1272 are each associated with a separate lumen 1274, 1276, as seen in FIGS. 38 and 39. Unlike the perforator 1160 illustrated in FIGS. 33 and 34, the two lumens 1274, 1276 are both enclosed in the cannula 1258. The apertures 1270 are spaced from each other, with the first aperture 1270 being disposed at the end 1252 of the perforator 1250, while the second aperture 1272 is disposed adjacent the flanges 1256.

As seen in FIG. 37, a second step of a two-shot molding process has been performed to define additional features of the perforator 1250. In particular, two gaskets 1280, 1282 have been formed. The first gasket 1280 is disposed at the first end 1252 of the perforator 1250 about the first aperture 1270. The gasket 1280 has a function similar to that of the seal 1170, described above: to seal a luer tip to the perforator 1250 to limit passage of fluid through other than the main lumen 1274. The second gasket 1282 is formed about the flanges 1256, and has an outwardly depending ring 1284 formed therewith, which ring 1284 will cooperate with an inner surface of a bore of a port assembly to form a fluid-tight seal therewith. Also formed with the gaskets 1280, 1282 is a valve 1286.

In particular, the valve 1286 is a one-way valve associated with the second aperture 1272. Thus, the valve 1286 is also associated with the secondary lumen 1276. The valve 1286, which may be referred to as a flap (or flapper) valve, is formed by separating the valve 1286 from the remainder of the molding along three of four sides of a rectangle, by cutting the molding along these three sides in a post-molding operation, for example. The fourth side forms a living hinge 1288, permitting the valve 1286 to pivot about the fourth side to open and close. Moreover, the living hinge 1288 may be designed to be prebiased in the direction of a closed state, and to bias the valve 1286 to the closed state even in the absence of a separate biasing mechanism.

The perforator 1250 would be incorporated into a port assembly 1300 according to the present disclosure as illustrated in FIGS. 38 and 39. The port assembly 1300 includes a housing 1302 with an opening 1304 and a bore 1306 therethrough. The opening 1304 is disposed at a first end 1308 of the housing 1302. An overmolded slit septum 1310 is disposed in the opening 1304 to control access through the opening 1304, and depends into the bore 1306. The cross-section of the bore 1306 may narrow slightly at the opening 1304 to define a rim 1312 with a shoulder 1314, against which the slit septum 1310 is disposed. The slit septum 1310 shaped as illustrated may be referred to as an inwardly-concave overmolded slit septum, as has been discussed in detail above.

A base 1320 is joined to the housing 1302 at the opposite end 1322 of the housing 1302 from the opening 1304, and has a membrane 1324 attached thereto. A resilient member 1326 is formed as a single structure with the membrane 1324, and depends along the bore 1306 from the end 1322 of the housing 1302 in the direction of the end 1308. The resilient member 1326 has an internal bore 1328 with a first and second ends 1330, 1332. The perforator 1250 is fitted into the bore 1328 of the resilient member 1326.

The operation of the port assembly 1300 is now explained with reference to FIGS. 38 and 39. A luer tip 1340 is inserted into the port assembly 1300 and through the septum 1310, advancing the perforator 1250 in the direction of the second end 1322 of the housing 1302. As best seen in FIG. 39, a space 1342 opens between the perforator 1250 and an inner surface 1344 of the housing 1302, creating a vacuum that pulls fluid into the space 1342. In particular, fluid is drawn through the lumen 1276 past the valve 1286, which is open as illustrated in FIG. 39.

As the luer tip 1340 is withdrawn, transitioning between a fully extended state illustrated in FIG. 39 and a standby state illustrated in FIG. 38, the perforator 1250 reverses direction. However, the luer tip 1340 will separate from the first end 1252 of the perforator 1250 and a gap will develop as explained above. The fluid is urged out of the space 1342 and passes through the gap between the luer tip 1340 and the first end of the perforator 1250 and into the lumen 1274. As a consequence, any medication in or about the port assembly 1300 will experience an automatic flush as the luer tip 1340 is withdrawn, leading to a reduction in the amount of medication in the lumen 1274 and in or about the port assembly 1300.

FIGS. 40-42 and 43-45 illustrate two additional perforators that may be substituted for the perforator 1250 in the port assembly 1300. As such, the discussion will concentrate on the perforators, rather than repeat the discussion regarding their placement and operation within the port assembly 1300. It is not believed that any modifications would be required to the other elements of the port assembly 1300 to utilize the perforators in FIGS. 40-45 in substitution for the perforator 1250.

Figure 40:
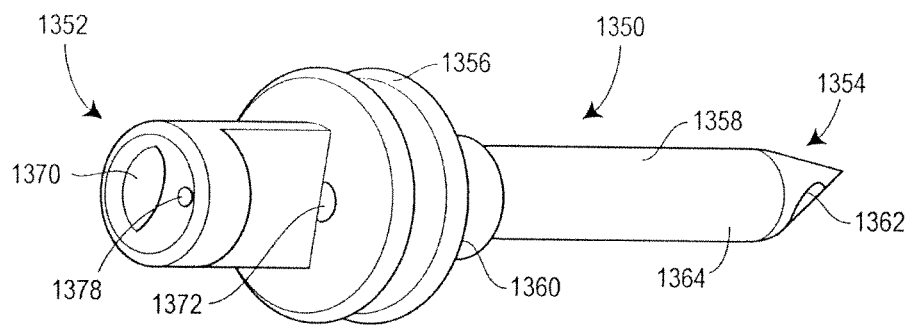
FIG. 40 is a perspective view of another perforator for use in a port assembly, such as illustrated in FIGS. 38 and 39, prior to a second step of a two-shot molding process.
Figure 41:
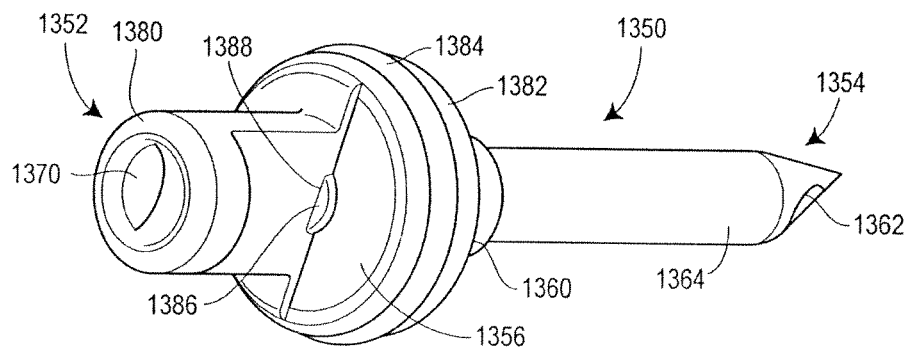
FIG. 41 is a perspective view of the perforator of FIG. 40 after the second step of the two-shot molding process to define a valve thereon.
Figure 42:
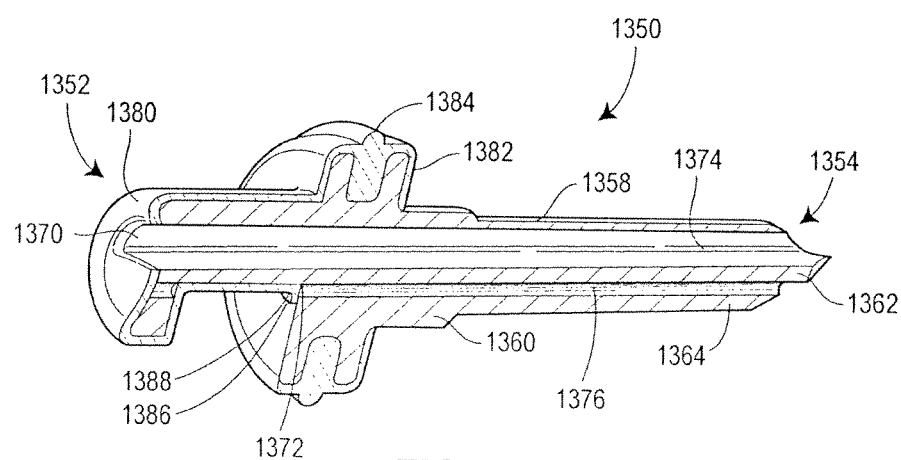
FIG. 42 is a cross-sectional view of the perforator of FIG. 40.

FIGS. 40-42 illustrate a first alternate perforator 1350 having a first end 1352 and a second end 1354. Disposed between the first and second ends 1352, 1354 are a pair of flanges 1356, although a single flange could have been included instead. A cannula 1358 is connected to the flanges 1356 at a first end 1360 and has pointed profile 1362 as a second end 1364.

Two apertures 1370, 1372 are formed at or near the first end 1352 of the perforator 1350. The two apertures 1370, 1372 are each associated with a separate lumen 1374, 1376, as seen in FIG. 42. The apertures 1370, 1372 are spaced from each other, with the first aperture 1370 being disposed at the end 1352 of the perforator 1350, while the second aperture 1372 is disposed adjacent the flanges 1356. A third aperture 1378 may also be provided at the first end 1352 of the perforator 1350 to facilitate the molding of the perforator 1350.

As seen in FIG. 41, a second step of a two-shot molding process has been performed to define additional features of the perforator 1350. In particular, two gaskets 1380, 1382 have been formed. The first gasket 1380 is disposed at the first end 1352 of the perforator 1350 about the first aperture 1370 to seal a luer tip to the perforator 1350. The second gasket 1382 is formed about the flanges 1356, and has an outwardly depending ring 1384 formed therewith to cooperate with an inner surface of a bore of a port assembly to form a fluid-tight seal therewith. Also formed with the gaskets 1380, 1382 is a valve 1386.

In particular, the valve 1386 is a one-way valve associated with the second aperture 1372. Thus, the valve 1386 is also associated with the secondary lumen 1376. The valve 1386, which may be referred to as a flap valve, is formed by separating the valve 1386 from the surface of the flange 1356. This may be performed by advancing a cutting blade parallel to the surface of the flange 1356 to separate the valve 1386 from the flange in a post-molding operation. A living hinge 1388 is thus formed, permitting the valve 1386 to pivot about the hinge 1388 to open and close and to be biased toward a closed state even in the absence of a separate biasing mechanism.

Figure 43:
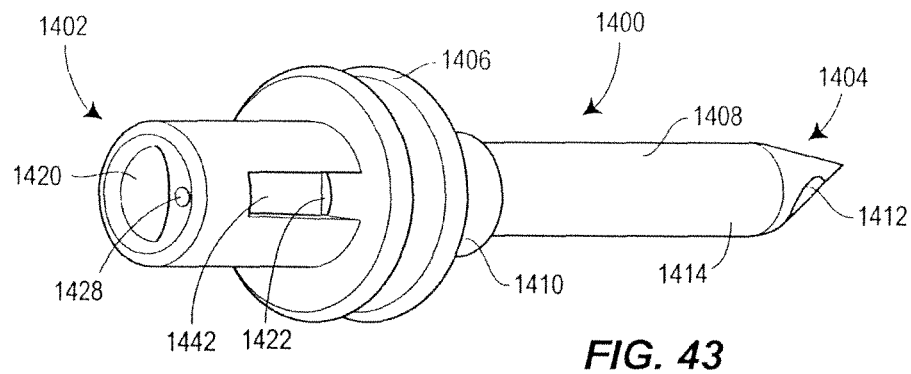
FIG. 43 is a perspective view of a further perforator for use in a port assembly, such as illustrated in FIGS. 38 and 39, prior to a second step of a two-shot molding process.
Figure 44:
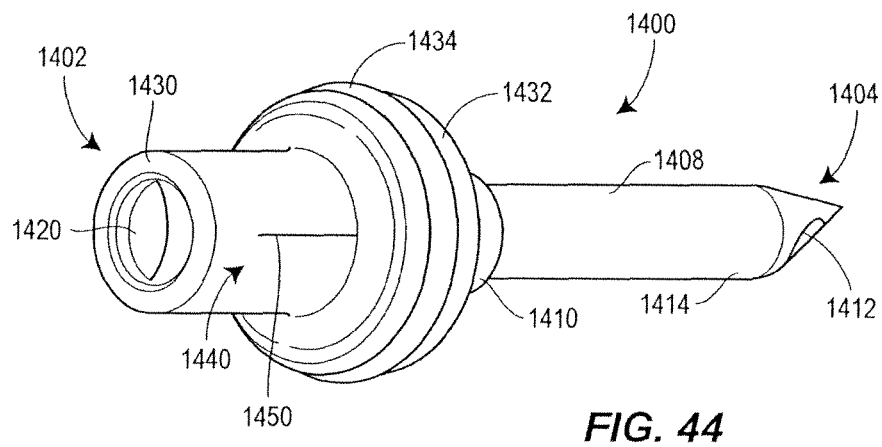
FIG. 44 is a perspective view of the perforator of FIG. 43 after the second step of the two-shot molding process to define a valve thereon.
Figure 45:
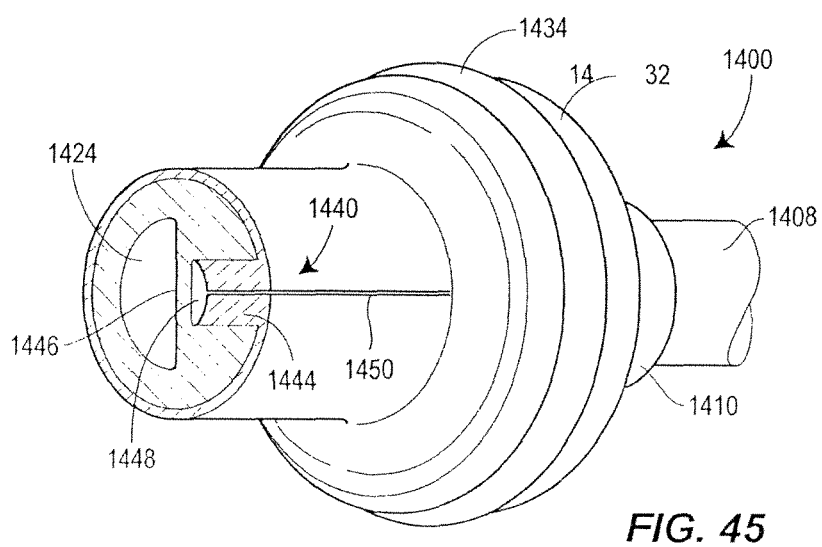
FIG. 45 is a cross-sectional view of the perforator of FIG. 43.

FIGS. 43-45 illustrate a second alternate perforator 1400 having a first end 1402 and a second end 1404. Disposed between the first and second ends 1402, 1404 are a pair of flanges 1406, although a single flange could have been included instead. A cannula 1408 is connected to the flanges 1406 at a first end 1410 and has pointed profile 1412 as a second end 1414.

Two apertures 1420, 1422 are formed at or near the first end 1402 of the perforator 1400. The two apertures 1420, 1422 are each associated with a separate lumen, one of which (1424) is illustrated in cross-section in FIG. 45. The apertures 1420, 1422 are spaced from each other, with the first aperture 1420 being disposed at the end 1402 of the perforator 1400, while the second aperture 1422 is disposed adjacent the flanges 1406. A third aperture 1428 may also be provided at the first end 1402 of the perforator 1400 to facilitate the molding of the perforator 1400, as was the case in regard to the perforator 1350.

As seen in FIG. 44, a second step of a two-shot molding process has been performed to define additional features of the perforator 1400. In particular, two gaskets 1430, 1432 have been formed. The first gasket 1430 is disposed at the first end 1402 of the perforator 1400 about the first aperture 1420 to seal a luer tip to the perforator 1400. The second gasket 1432 is formed about the flanges 1406, and has an outwardly depending ring 1434 formed therewith to cooperate with an inner surface of a bore of a port assembly to form a fluid-tight seal therewith. Also formed with the gaskets 1430, 1432 is a valve 1440.

In particular, the valve 1440 is a slit valve that operates to open and close according to different differential pressures that exist across the valve. In particular, the valve 1440 is formed in a groove 1442 (as seen in FIGS. 43 and 45) that is in communication with the aperture 1422. The groove 1442 is covered in the second step of the two-shot molding process with a wall 1444, the thickness of which may be exaggerated in FIG. 45 to facilitate illustration of the elements of the valve 1440. In a post-molding operation, a cutting blade is advanced toward the longitudinal axis of the perforator 1400 in the direction of a wall 1446. A pin may be disposed along the wall 1446 to define a passage 1448 in communication with the aperture 1422, and to cooperate with the cutting blade to form a slit 1450 in the wall 1444.

As mentioned above, the differential pressures across the slit 1450 will cause the valve 1440 to open to permit fluid flow across the barrier defined by the wall 1446. In particular, a neutral differential pressure will maintain the valve 1440 in a closed state. If the differential pressure of the fluid in the passage 1448 relative to the space beyond the wall 1446 exceeds a first cracking pressure, the slit 1450 will open and fluid will be permitted to flow through the slit 1450 past the wall 1444. According to certain embodiments, if the differential pressure of the fluid in the passage 1448 drops below a second cracking pressure, the slit will open and be permitted to flow through the slit 1450 into the passage 1448. However, according to the dimensions and structure (e.g. curvature) of the wall 1444 and the slit 1450, the second cracking pressure may set so that over a range of normal operating pressures, the valve 1440 acts essentially as a one-way valve, permitting fluid to flow from the passage 1448 through the slit 1450 while limiting fluid flow along the reverse path. Alternatively, depending on size of the volume ratio referred to above, some degree of backflow through the valve 1440 may be permissible during flushing.

We claim:

1. A fluid container comprising:
a receptacle for retaining a fluid;
at least one conduit in communication with the receptacle; and
the at least one conduit defined, at least in part, by a port assembly,
the port assembly including a housing with an opening and a bore therethrough, a slit septum disposed in the opening to control access through the opening, a base joined to the housing and having a membrane attached thereto, a perforator having a first end abutting the slit septum and a second end aligned with the membrane, and a resilient member disposed between the perforator and the base,
the perforator having first and second lumens, the first lumen extending between the first and second ends of the perforator and the second lumen extending between a point between the first and second ends and the second end, a seal disposed about the first lumen at the first end of the perforator and a one-way valve connected to the second lumen to limit flow of fluid through the second lumen in the direction of the second end and permit flow of fluid through the second lumen in the direction of the first end.

2. The fluid container according to claim 1, wherein the port assembly comprises a space defined between the perforator and an inner surface of the housing with the first end of the perforator spaced from the slit septum, the ratio of volume within the space being greater than 3:1 relative to volume within the first lumen.

3. The fluid container according to claim 2, wherein the perforator includes a flange disposed between the first and second ends, and a gasket overmolded on the flange, the gasket abutting the bore of the housing.

4. The fluid container according to claim 2, wherein the ratio of volume within the space is 8:1 relative to volume within the first lumen.

5. The fluid container according to claim 1, wherein the valve comprises a flap valve.

6. The fluid container according to claim 1, wherein the valve comprises a slit valve that operates to open and close according to a differential pressure across the valve.

7. The fluid container according to claim 1, wherein the perforator has an outer surface, and the second lumen is formed at least partially on the outer surface of the perforator.

8. The fluid container according to claim 1, wherein the perforator comprises a cannula, and the first and second lumens are enclosed within the cannula.

9. The fluid container according to claim 1, wherein the cross-section of the first lumen is larger than the cross-section of the second lumen.

10. The fluid container according to claim 1, wherein the fluid container comprises a gondola, the base formed integrally with the gondola and defining the at least one conduit.

11. The fluid container according to claim 1, wherein the fluid container comprises a port tube, the base disposed in the port tube to define the at least one conduit.

12. A port assembly to be used in a conduit of a fluid container, the port assembly comprising:
a housing with an opening and a bore therethrough,
a slit septum disposed in the opening to control access through the opening,
a base joined to the housing and having a membrane attached thereto,
a perforator having a first end abutting the slit septum and a second end aligned with the membrane,
the perforator also having first and second lumens, the first lumen extending between the first and second ends of the perforator and the second lumen extending between a point between the first and second ends and the second end, a seal disposed about the first lumen at the first end of the perforator and a one-way valve connected to the second lumen to limit flow of fluid through the second lumen in the direction of the second end and permit flow of fluid through the second lumen in the direction of the first end; and
a resilient member disposed between the perforator and the base.

13. The port assembly according to claim 12, wherein the port assembly comprises a space defined between the perforator and an inner surface of the housing with the first end of the perforator spaced from the slit septum, the ratio of volume within the space being greater than 3:1 relative to volume within the first lumen.

14. The port assembly according to claim 13, wherein the perforator includes a flange disposed between the first and second ends, and a gasket overmolded on the flange, the gasket abutting the bore of the housing.

15. The port assembly according to claim 13, wherein the ratio of volume within the space is 8:1 relative to volume within the first lumen.

16. The port assembly according to claim 12, wherein the valve comprises a flap valve.

17. The port assembly according to claim 12, wherein the valve comprises a slit valve that operates to open and close according to a differential pressure across the valve.

* * * * *